(12) United States Patent
Wagenbach et al.

(10) Patent No.: US 11,793,438 B2
(45) Date of Patent: *Oct. 24, 2023

(54) NEURAL SENSING IN AN IMPLANTABLE STIMULATOR DEVICE DURING THE PROVISION OF ACTIVE STIMULATION

(71) Applicant: Boston Scientific Neuromodulation Corporation, Valencia, CA (US)

(72) Inventors: David M. Wagenbach, Simi Valley, CA (US); Kiran K. Gururaj, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 57 days.

This patent is subject to a terminal disclaimer.

(21) Appl. No.: 17/648,660

(22) Filed: Jan. 21, 2022

(65) Prior Publication Data

US 2022/0142539 A1 May 12, 2022

Related U.S. Application Data

(63) Continuation of application No. 16/821,617, filed on Mar. 17, 2020, now Pat. No. 11,259,733.
(Continued)

(51) Int. Cl.
*A61N 1/36* (2006.01)
*A61N 1/02* (2006.01)
(Continued)

(52) U.S. Cl.
CPC ............... *A61B 5/24* (2021.01); *A61B 5/686* (2013.01); *A61B 5/7217* (2013.01); *A61N 1/36139* (2013.01); *A61B 2562/0209* (2013.01)

(58) Field of Classification Search
CPC . A61B 2562/0209; A61B 5/24; A61B 5/4836; A61B 5/686; A61B 5/7217;
(Continued)

(56) References Cited

U.S. PATENT DOCUMENTS 5,697,958 A  12/1997  Paul et al.
5,702,429 A  12/1997  King
(Continued)

FOREIGN PATENT DOCUMENTS

WO  2015/077362  5/2015
WO  2017/100866  6/2017
(Continued)

OTHER PUBLICATIONS

International Search Report and Written Opinion regarding corresponding PCT application No. PCT/US2020/023184, dated Jun. 18, 2020.

*Primary Examiner* — Jon Eric C Morales
(74) *Attorney, Agent, or Firm* — Lewis & Reese, PLLC

(57) ABSTRACT

Techniques for sensing neural responses such as Evoked Compound Action Potentials (ECAPs) in an implantable stimulator device are disclosed. A first therapeutic pulse phase is followed by a second pulse phase, which phases may be of opposite polarities to assist with active charge recovery. The second pulse phase is formed so as to overlap in time with the arrival of the ECAP at a sensing electrode, which second phase may generally be longer and of a lower amplitude. In so doing, a stimulation artifact formed in a patient's tissue is rendered constant, and of a smaller amplitude, when the ECAP is sensed at the sensing electrode, which eases sensing by a sense amp circuit. Passive charge recovery may follow the second phase, which will not interfere with ECAP sensing that has already occurred.

20 Claims, 11 Drawing Sheets

Related U.S. Application Data

(60) Provisional application No. 62/825,982, filed on Mar. 29, 2019.

(51) Int. Cl.
*A61B 5/24* (2021.01)
*A61B 5/00* (2006.01)

(58) Field of Classification Search
CPC ............ A61N 1/36062; A61N 1/36125; A61N 1/36135; A61N 1/36139
See application file for complete search history.

(56) References Cited

U.S. PATENT DOCUMENTS

| | | | |
|---|---|---|---|
| 5,902,236 A | 5/1999 | Iversen | |
| 5,902,249 A | 5/1999 | Lyster | |
| 5,913,882 A | 6/1999 | King | |
| 6,181,969 B1 | 1/2001 | Gord | |
| 6,516,227 B1 | 2/2003 | Meadows et al. | |
| 7,024,247 B2 | 4/2006 | Gliner et al. | |
| 7,424,322 B2 | 9/2008 | Lombardi et al. | |
| 7,450,992 B1 | 11/2008 | Cameron | |
| 8,255,057 B2 | 8/2012 | Fang et al. | |
| 8,335,664 B2 | 12/2012 | Eberle | |
| 8,352,030 B2 | 1/2013 | Denison | |
| 8,606,362 B2 | 12/2013 | He et al. | |
| 8,620,436 B2 | 12/2013 | Parramon et al. | |
| 9,044,155 B2 | 6/2015 | Strahl | |
| 9,155,892 B2 | 10/2015 | Parker et al. | |
| 9,248,274 B2 | 2/2016 | Troosters et al. | |
| 9,248,279 B2 | 2/2016 | Chen et al. | |
| 9,265,431 B2 | 2/2016 | Hincapie Ordonez et al. | |
| 9,302,112 B2 | 4/2016 | Bornzin et al. | |
| 9,381,356 B2 | 7/2016 | Parker et al. | |
| 9,386,934 B2 | 7/2016 | Parker et al. | |
| 9,403,013 B2 | 8/2016 | Walker et al. | |
| 9,409,020 B2 | 8/2016 | Parker | |
| 9,526,897 B2 | 12/2016 | Chen et al. | |
| 9,533,148 B2 | 1/2017 | Carcieri | |
| 9,731,116 B2 | 8/2017 | Chen | |
| 9,872,990 B2 | 1/2018 | Parker et al. | |
| 9,974,455 B2 | 5/2018 | Parker et al. | |
| 10,076,667 B2 | 9/2018 | Kaula et al. | |
| 11,259,733 B2 * | 3/2022 | Wagenbach | A61N 1/36139 |
| 2002/0156513 A1 | 10/2002 | Borkan | |
| 2005/0246004 A1 | 11/2005 | Cameron et al. | |
| 2008/0146894 A1 | 6/2008 | Bulkes et al. | |
| 2012/0092031 A1 | 4/2012 | Shi et al. | |
| 2012/0095519 A1 | 4/2012 | Parramon et al. | |
| 2012/0095529 A1 | 4/2012 | Parramon et al. | |
| 2013/0289665 A1 | 10/2013 | Marnfeldt et al. | |
| 2014/0194772 A1 | 7/2014 | Single et al. | |
| 2014/0236042 A1 | 8/2014 | Parker et al. | |
| 2014/0296737 A1 | 10/2014 | Parker et al. | |
| 2015/0119751 A1 | 4/2015 | Stanslaski et al. | |
| 2015/0157861 A1 | 6/2015 | Aghassian | |
| 2015/0282725 A1 | 10/2015 | Single | |
| 2015/0313487 A1 | 11/2015 | Single et al. | |
| 2016/0166164 A1 | 6/2016 | Obradovic et al. | |
| 2016/0287126 A1 | 10/2016 | Parker et al. | |
| 2016/0287182 A1 | 10/2016 | Single | |
| 2017/0049345 A1 | 2/2017 | Single | |
| 2017/0071490 A1 | 3/2017 | Parker et al. | |
| 2017/0135624 A1 | 5/2017 | Parker | |
| 2017/0216587 A1 | 8/2017 | Parker | |
| 2017/0296823 A1 | 10/2017 | Hershey et al. | |
| 2017/0361101 A1 | 12/2017 | Single | |
| 2018/0071527 A1 | 3/2018 | Feldman et al. | |
| 2018/0110987 A1 | 4/2018 | Parker | |
| 2018/0117335 A1 | 5/2018 | Parker et al. | |
| 2018/0132747 A1 | 5/2018 | Parker et al. | |
| 2018/0132760 A1 | 5/2018 | Parker | |
| 2018/0133459 A1 | 5/2018 | Parker et al. | |
| 2018/0140831 A1 | 5/2018 | Feldman et al. | |
| 2018/0228391 A1 | 8/2018 | Parker et al. | |
| 2018/0228547 A1 | 8/2018 | Parker et al. | |
| 2018/0256052 A1 | 9/2018 | Parker et al. | |
| 2019/0099602 A1 | 4/2019 | Esteller et al. | |
| 2019/0175915 A1 | 6/2019 | Brill et al. | |
| 2019/0209844 A1 | 7/2019 | Esteller et al. | |
| 2019/0275331 A1 | 9/2019 | Zhu | |
| 2019/0290900 A1 | 9/2019 | Esteller et al. | |
| 2019/0299006 A1 | 10/2019 | Marnfeldt | |
| 2019/0366094 A1 | 12/2019 | Esteller et al. | |
| 2020/0061380 A1 | 2/2020 | Zhang et al. | |
| 2020/0155019 A1 | 5/2020 | Esteller et al. | |

FOREIGN PATENT DOCUMENTS

| | | |
|---|---|---|
| WO | 2017/173493 | 10/2017 |
| WO | 2017/210352 | 12/2017 |
| WO | 2017/219096 | 12/2017 |

* cited by examiner

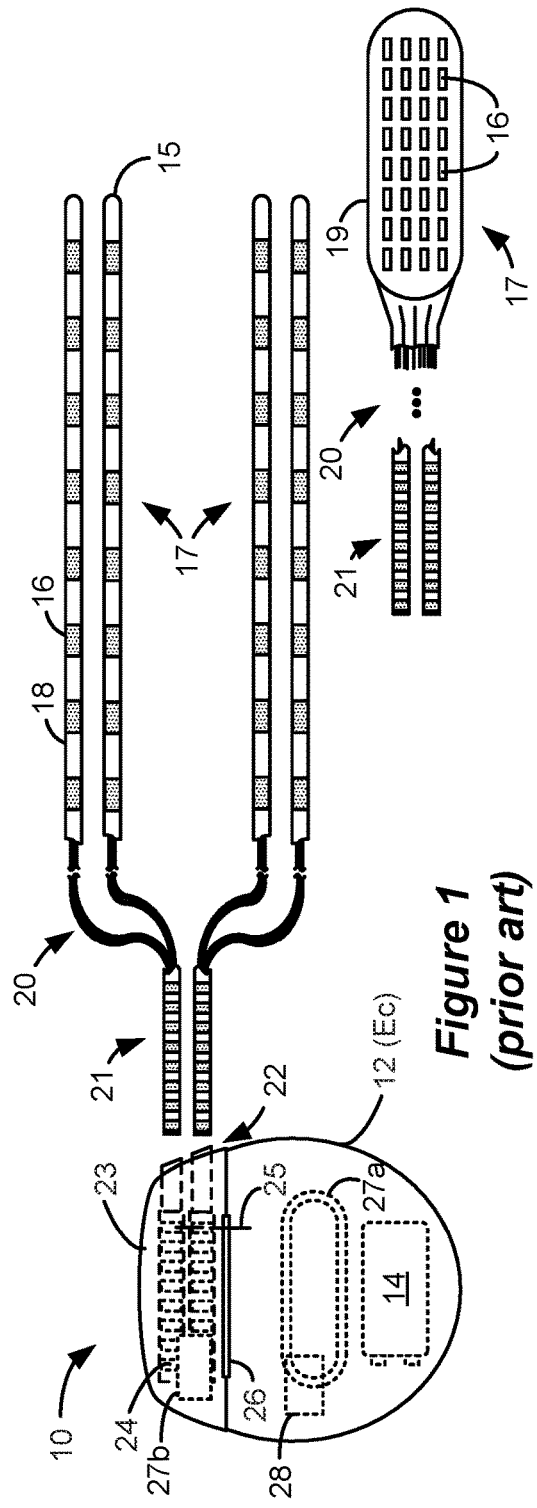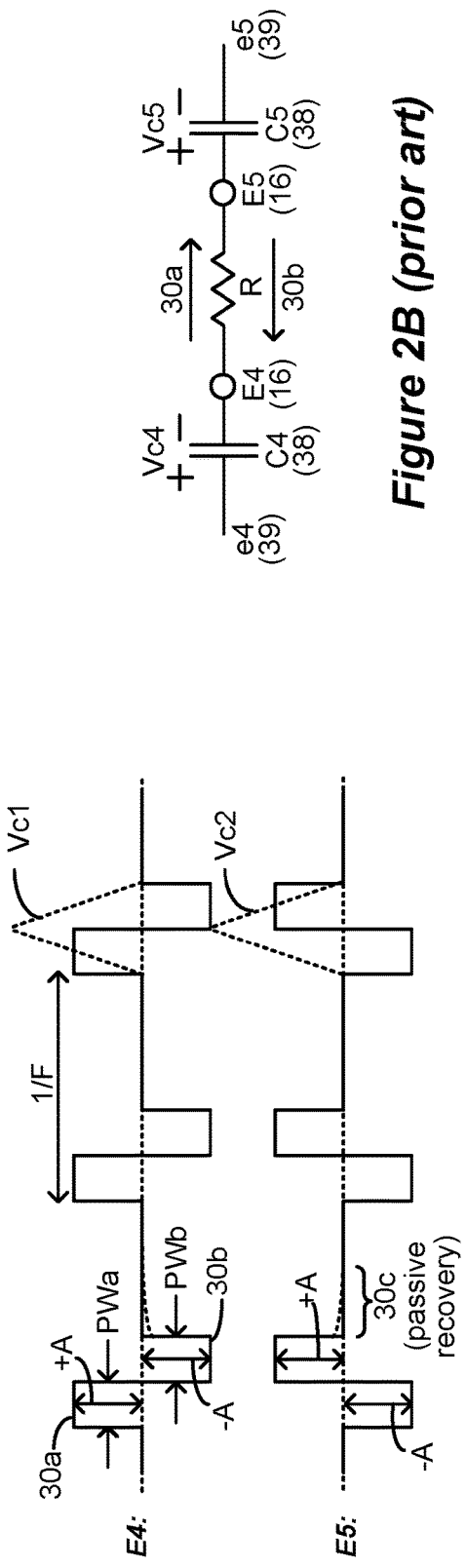

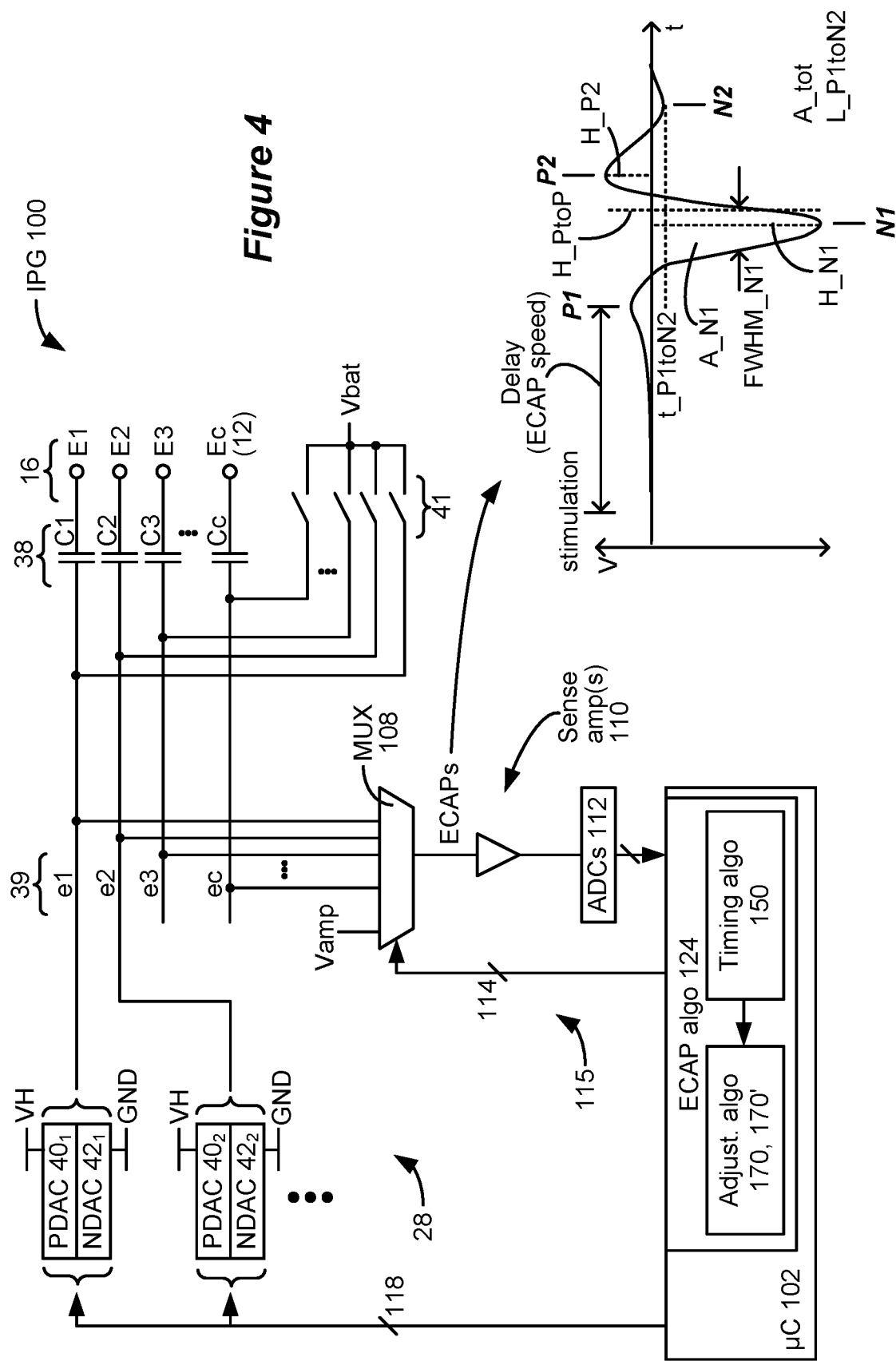

NEURAL SENSING IN AN IMPLANTABLE STIMULATOR DEVICE DURING THE PROVISION OF ACTIVE STIMULATION

CROSS REFERENCE TO RELATED APPLICATIONS

This is a continuation of U.S. patent application Ser. No. 16/821,617, filed Mar. 17, 2020, which is a non-provisional of U.S. Provisional Patent Application Ser. No. 62/825,982, filed Mar. 29, 2019. These applications are incorporated herein by reference in their entireties, and priority is claimed to them.

FIELD OF THE INVENTION

This application relates to Implantable Medical Devices (IMDs), and more specifically to circuitry to assist with sensing neural signals in an implantable stimulator device.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application specific and therefore can vary. The conductive case 12 can also comprise an electrode (Ec). In a SCS application, the electrode lead(s) are typically implanted in the spinal column proximate to the dura in a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22. In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. The goal of SCS therapy is to provide electrical stimulation from the electrodes 16 to alleviate a patient's symptoms, such as chronic back pain.

IPG 10 can include an antenna 27a allowing it to communicate bi-directionally with a number of external devices used to program or monitor the IPG, such as a hand-held patient controller or a clinician's programmer, as described for example in U.S. Patent Application Publication 2019/0175915. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Zigbee, MICS, and the like.

Stimulation in IPG 10 is typically provided by pulses each of which may include a number of phases such as 30a and 30b, as shown in the example of FIG. 2A. Stimulation parameters typically include amplitude (current I, although a voltage amplitude V can also be used); frequency (F); pulse width (PW) of the pulses or of its individual phases; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E4 has been selected as an anode (during its first phase 30a), and thus provides pulses which source a positive current of amplitude +A to the tissue. Electrode E5 has been selected as a cathode (again during first phase 30a), and thus provides pulses which sink a corresponding negative current of amplitude −A from the tissue. This is an example of bipolar stimulation, in which only two lead-based electrodes are used to provide stimulation to the tissue (one anode, one cathode). However, more than one electrode may be selected to act as an anode at a given time, and more than one electrode may be selected to act as a cathode at a given time.

IPG 10 as mentioned includes stimulation circuitry 28 to form prescribed stimulation at a patient's tissue. FIG. 3 shows an example of stimulation circuitry 28, which includes one or more current source circuits $40_i$ and one or more current sink circuits $42_i$. The sources and sinks $40_i$ and $42_i$ can comprise Digital-to-Analog converters (DACs), and may be referred to as PDACs $40_i$ and NDACs $42_i$ in accordance with the Positive (sourced, anodic) and Negative (sunk, cathodic) currents they respectively issue. In the example shown, a NDAC/PDAC $40_i/42_i$ pair is dedicated (hardwired) to a particular electrode node ei 39. Each electrode node ei 39 is connected to an electrode Ei 16 via a DC-blocking capacitor Ci 38, for the reasons explained below. The stimulation circuitry 28 in this example also supports selection of the conductive case 12 as an electrode (Ec 12), which case electrode is typically selected for monopolar stimulation. PDACs $40_i$ and NDACs $42_i$ can also comprise voltage sources.

Proper control of the PDACs $40_i$ and NDACs $42_i$ allows any of the electrodes 16 to act as anodes or cathodes to create a current through a patient's tissue, R, hopefully with good therapeutic effect. In the example shown (FIG. 2A), and during the first phase 30a in which electrodes E4 and E5 are selected as an anode and cathode respectively, PDAC $40_4$ and NDAC $42_5$ are activated and digitally programmed to produce the desired current, A, with the correct timing (e.g., in accordance with the prescribed frequency F and pulse widths PWa). During the second phase 30b (PWb), PDAC $40_5$ and NDAC $42_4$ would be activated to reverse the polarity of the current. More than one anode electrode and more than one cathode electrode may be selected at one time, and thus current can flow through the tissue R between two or more of the electrodes 16.

Power for the stimulation circuitry 28 is provided by a compliance voltage VH. As described in further detail in U.S. Patent Application Publication 2013/0289665, the compliance voltage VH can be produced by a compliance voltage generator 29, which can comprise a circuit used to boost the battery 14's voltage (Vbat) to a voltage VH sufficient to drive the prescribed current A through the tissue R. The compliance voltage generator 29 may comprise an inductor-based boost converter as described in the '665 Publication, or can comprise a capacitor-based charge pump. Because the resistance of the tissue is variable, VH may also be variable, and can be as high as 18 Volts in one example.

Other stimulation circuitries 28 can also be used in the IPG 10. In an example not shown, a switching matrix can intervene between the one or more PDACs $40_i$ and the electrode nodes ei 39, and between the one or more NDACs $42_i$ and the electrode nodes. Switching matrices allows one or more of the PDACs or one or more of the NDACs to be connected to one or more anode or cathode electrode nodes at a given time. Various examples of stimulation circuitries can be found in U.S. Pat. Nos. 6,181,969, 8,606,362, 8,620, 436, and U.S. Patent Application Publications 2018/0071520 and 2019/0083796. Much of the stimulation circuitry 28 of FIG. 3, including the PDACs $40_i$ and NDACs $42_i$, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519, which are incorporated by reference. As explained in these references, ASIC(s) may also contain other circuitry useful in the IPG 10, such as telemetry circuitry (for interfacing off chip with telemetry antennas 27a and/or 27b), the compliance voltage generator 29, various measurement circuits, etc.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

Although not shown, circuitry in the IPG 10 including the stimulation circuitry 28 can also be included in an External Trial Stimulator (ETS) device which is used to mimic operation of the IPG during a trial period and prior to the IPG 10's implantation. An ETS device is typically used after the electrode array 17 has been implanted in the patient. The proximal ends of the leads in the electrode array 17 pass through an incision in the patient and are connected to the externally-worn ETS, thus allowing the ETS to provide stimulation to the patient during the trial period. Further details concerning an ETS device are described in U.S. Pat. No. 9,259,574 and U.S. Patent Application Publication 2019/0175915.

Referring again to FIG. 2A, the stimulation pulses as shown are biphasic, with each pulse at each electrode comprising a first phase 30a followed thereafter by a second phase 30b of opposite polarity. (Although not shown, but as is well known, a short interphase period may intervene between the phases 30a and 30b during which no current is actively driven by the DAC circuitry 40/42, which allows the DAC circuitry time to transition between the phases). Biphasic pulses are useful to actively recover any charge that might be stored on capacitive elements in the electrode current paths, such as the DC-blocking capacitors 38, the electrode/tissue interface, or within the tissue itself. To recover all charge by the end of the second pulse phase 30b of each pulse (Vc4=Vc5=0V), the first and second phases 30a and 30b are preferably charged balanced at each electrode, with the phases comprising an equal amount of charge but of the opposite polarity. In the example shown, such charge balancing is achieved by using the same pulse width (PWa=PWb) and the same amplitude (|+A|=|−A|) for each of the pulse phases 30a and 30b. However, the pulse phases 30a and 30b may also be charged balance if the product of the amplitude and pulse widths of the two phases 30a and 30b are equal, as is known.

FIG. 3 shows that stimulation circuitry 28 can include passive recovery switches $41_i$, which are described further in U.S. Patent Application Publications 2018/0071527 and 2018/0140831. Passive recovery switches $41_i$ may be attached to each of the electrode nodes 39, and are used to passively recover any charge remaining on the DC-blocking capacitors Ci 38 after issuance of the second pulse phase 30b—i.e., to recover charge without actively driving a current using the DAC circuitry. Passive charge recovery can be prudent, because non-idealities in the stimulation circuitry 28 may lead to pulse phases 30a and 30b that are not perfectly charge balanced. Passive charge recovery typically occurs after actively-driven phases 30a and 30b have completed, and during at least a portion 30c (FIG. 2A) of the quiet periods between the pulses, by closing passive recovery switches $41_i$. As shown in FIG. 3, the other end of the switches $41_i$ not coupled to the electrode nodes 39 are connected to a common reference voltage, which in this example comprises the voltage of the battery 14, Vbat, although another reference voltage could be used. As explained in the above-cited references, passive charge recovery tends to equilibrate the charge on the DC-blocking capacitors 38 and other capacitive elements by placing the capacitors in parallel between the reference voltage (Vbat) and the patient's tissue. Note that passive charge recovery is illustrated as small exponentially-decaying curves during 30c in FIG. 2A, which may be positive or negative depending on whether pulse phase 30a or 30b has a predominance of charge at a given electrode.

SUMMARY

A stimulator device is disclosed, which may comprise: a plurality of electrode nodes, each electrode node configured to be coupled to one of a plurality of electrodes configured to contact a patient's tissue; stimulation circuitry programmed to form stimulation at at least two of the electrode nodes, wherein the stimulation at each of the two electrode nodes comprises a pulse comprising a first phase followed by a second phase; and sensing circuitry configured to sense a neural response to the stimulation at a sensing electrode node comprising one of the electrode nodes, wherein the neural response is present at the sensing electrode node for a duration, wherein the sensing circuitry is configured to sense the neural response during the second phase.

In one example, the sensing electrode node is selectable from one of the electrode nodes. In one example, the sensing circuitry is configured to sense the entire duration of the neural response during the second phase. In one example, the sensing circuitry comprises a differential amplifier, and wherein the differential amplifier receives the sensing electrode node at a first input, and wherein the differential amplifier receives a reference electrode node selected from one of the electrode nodes at a second input. In one example, the device further comprise a conductive case for housing the stimulation circuitry and the sensing circuitry, wherein the conductive case comprises one of the plurality of electrodes, and wherein the case electrode is coupled to the reference electrode node. In one example, the first phase is of an opposite polarity to the second phase at each of the at least two electrode nodes. In one example, the first and second phases are charge balanced at each of the at least two electrodes. In one example, the first and second phases are not charge balanced at each of the at least two electrodes. In one example, the device further comprises control circuitry configured with at least one algorithm, wherein the at least one algorithm is configured to determine when the neural response will be present at the sensing electrode node for the duration. In one example, the at least one algorithm is further configured to time the second phase at the at least two electrode nodes such that the second phase will entirely overlap the neural response at the sensing electrode node for the duration. In one example, the algorithm is further configured to determine an amplitude of the second phase. In one example, the algorithm is further configured to determine the amplitude of the second phase such that the second phase is charge balanced with the first phase at each of the at least two electrodes nodes. In one example, the stimulation circuitry comprises digital-to-analog circuitry configured to actively drive a current, wherein the second phase is actively driven by the digital-to-analog circuitry at each of the at least two electrode nodes. In one example, the second phase is actively driven with a constant current. In one example, the first phase is actively driven by the digital-to-analog circuitry at each of the at least two electrode nodes. In one example, the first and second phases are actively driven by the digital-to-analog circuitry with constant currents, wherein an amplitude of the constant current during the first phase is larger than an amplitude of the constant current during the second phase at each of the at least two electrode nodes. In one example, the second phase comprises sub-phases of different amplitudes, wherein the sensing circuitry is configured to sense the neural response only during one of the sub-phases. In one example, the sensing circuitry is configured to sense the neural response only during one of the sub-phases having a lowest amplitude. In one example, the amplitude of the lowest amplitude sub-phase is constant. In one example, the stimulation circuitry comprises a plurality of passive charge recovery switches each coupled between one of the electrode nodes and a reference potential. In one example, the stimulation circuitry is further programmed to provide passive charge recovery after the second phase by closing at least the passive recovery switches coupled to the at least two electrode nodes. In one example, the stimulation circuitry is further programmed to provide passive charge recovery between the first and second phases by closing at least the passive recovery switches coupled to the at least two electrode nodes. In one example, the stimulation circuitry is programmed to form a sequence of the pulses at the at least two of the electrodes nodes. In one example, the first phases are of opposite polarities at the at least two of the electrodes nodes, and wherein the second phases are of opposite polarities at the at least two of the electrodes nodes. In one example, each electrode node is coupled to its associated electrode through a DC-blocking capacitor. In one example, the stimulator device comprises an implantable pulse generator or an external trial stimulator.

A method is disclosed for operating a stimulator device, the stimulator device comprising a plurality of electrode nodes, each electrode node configured to be coupled to one of a plurality of electrodes configured to contact a patient's tissue. The method may comprise: providing stimulation at at least two of the electrode nodes, wherein the stimulation at each of the two electrode nodes comprises at least one pulse comprising a first phase followed by a second phase; and sensing a neural response to the stimulation at a sensing electrode node comprising one of the electrode nodes, wherein the neural response is present at the sensing electrode node for a duration, wherein the sensing circuitry is configured to sense the neural response during the second phase.

In one example, the method further comprises selecting the sensing electrode node from one of the electrode nodes. In one example, the entire duration of the neural response is sensed during the second phase. In one example, the sensing circuitry comprises a differential amplifier, and wherein the differential amplifier receives the sensing electrode node at a first input, and wherein the differential amplifier receives a reference electrode node selected from one of the electrode nodes at a second input. In one example, the stimulator device further comprises a conductive case, wherein the conductive case comprises one of the plurality of electrodes, and wherein the case electrode is coupled to the reference electrode node. In one example, the first phase is of an opposite polarity to the second phase at each of the at least two electrode nodes. In one example, the first and second phases are charge balanced at each of the at least two electrodes. In one example, the first and second phases are not charge balanced at each of the at least two electrodes. In one example, the method further comprises determining using control circuitry in the stimulator device when the neural response will be present at the sensing electrode node for the duration. In one example, the second phase is timed at the at least two electrode nodes such that the second phase will entirely overlap the neural response at the sensing electrode node for the duration. In one example, the method further comprises determining an amplitude of the second phase. In one example, the method further comprises determine the amplitude of the second phase such that the second phase is charge balanced with the first phase at each of the at least two electrodes nodes. In one example, the second phase is actively driven by digital-to-analog circuitry in the stimulator device at each of the at least two electrode nodes. In one example, the second phase is actively driven with a constant current. In one example, the first phase is actively driven by the digital-to-analog circuitry at each of the at least two electrode nodes. In one example, the first and second phases are actively driven by the digital-to-analog circuitry with constant currents, wherein an amplitude of the constant current during the first phase is larger than an amplitude of the constant current during the second phase at each of the at least two electrode nodes. In one example, the second phase comprises sub-phases of different amplitudes, wherein the neural response is sensed only during one of the sub-phases. In one example, the neural response is sensed only during one of the sub-phases having a lowest amplitude. In one example, the amplitude of the lowest amplitude sub-phase is constant. In one example, the method further comprises providing passive charge recovery after the second phase by closing passive recovery switches coupled at least to the at least two electrode nodes. In one example, the method further comprises providing passive charge recovery between the first and second phases by closing passive recovery switches coupled at least to the at least two electrode nodes. In one example, the stimulation comprises a sequence of the pulses at the at least two of the electrodes nodes. In one example, the first phases are of opposite polarities at the at least two of the electrodes nodes, and wherein the second phases are of opposite polarities at the at least two of the electrodes nodes. In one example, each electrode node is coupled to its associated electrode through a DC-blocking capacitor. In one example, the stimulator device comprises an implantable pulse generator or an external trial stimulator.

BRIEF DESCRIPTION OF THE DRAWINGS

FIG. 1 shows an Implantable Pulse Generator (IPG), in accordance with the prior art.

FIGS. 2A and 2B show an example of stimulation pulses producible by the IPG, in accordance with the prior art.

FIG. 4 shows an improved IPG having neural response sensing, and the ability to adjust stimulation dependent on such sensing.

FIG. 6A shows a neural response as ideally sensed at a sensing electrode, while

DETAILED DESCRIPTION

An increasingly interesting development in pulse generator systems, and in Spinal Cord Stimulator (SCS) pulse generator systems specifically, is the addition of sensing capability to complement the stimulation that such systems provide. For example, and as explained in U.S. Patent Application Publication 2017/0296823, it can be beneficial to sense a neural response in neural tissue that has received stimulation from an SCS pulse generator. One such neural response is an Evoked Compound Action Potential (ECAP). An ECAP comprises a cumulative response provided by neural fibers that are recruited by the stimulation, and essentially comprises the sum of the action potentials of recruited fibers when they "fire." An ECAP is shown in FIG. 4, and comprises a number of peaks that are conventionally labeled with P for positive peaks and N for negative peaks, with P1 comprising a first positive peak, N1 a first negative peak, P2 a second positive peak and so on. Note that not all ECAPs will have the exact shape and number of peaks as illustrated in FIG. 4, because an ECAP's shape is a function of the number and types of neural fibers that are recruited and that are involved in its conduction. An ECAP is generally a small signal, and may have a peak-to-peak amplitude on the order of tens of microVolts to tens of milliVolts.

Also shown in FIG. 4 is circuitry for an IPG 100 that is capable of providing stimulation and sensing a resulting ECAP or other neural response or signal. The IPG 100 includes control circuitry 102, which may comprise a microcontroller for example such as Part Number MSP430, manufactured by Texas Instruments, which is described in data sheets at http://www.ti.com/1sds/ti/microcontroller/16-bit msp430/overview.page? DCMP=MCU_other& HQS' msp430, which is incorporated herein by reference. Other types of controller circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs), such as those described earlier. The disclosed circuitry and techniques can also be implemented in an ETS implantable stimulator, although this isn't further discussed.

Figure 3:
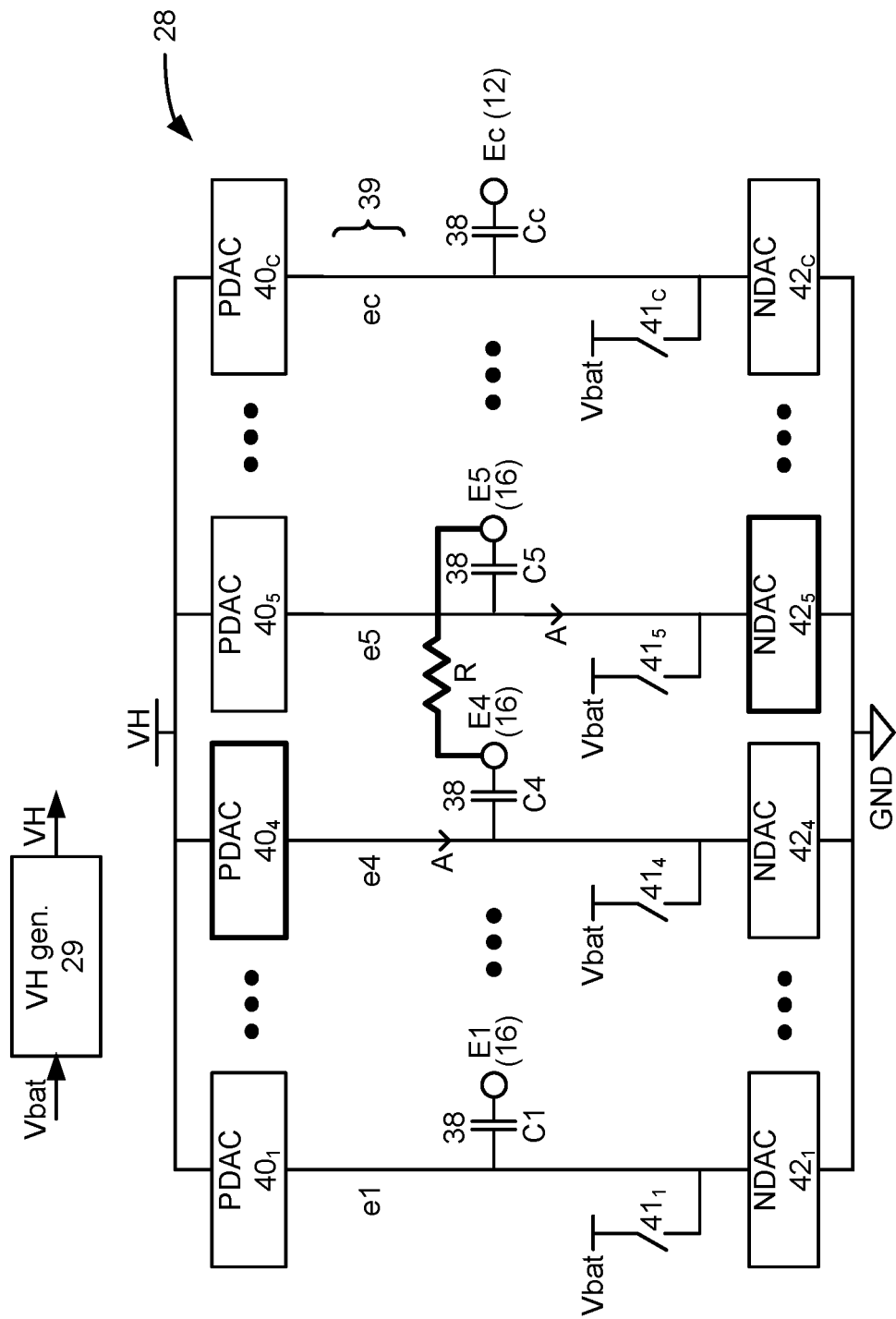
FIG. 3 shows stimulation circuitry useable in the IPG, in accordance with the prior art.

The IPG 100 also includes stimulation circuitry 28 to produce stimulation at the electrodes 16, which may comprise the stimulation circuitry 28 shown earlier (FIG. 3). A bus 118 provides digital control signals from the control circuitry 102 (and possibly from an ECAP algorithm 124, described below) to one or more PDACs $40_i$ or NDACs $42_j$ to produce currents or voltages of prescribed amplitudes (A) for the stimulation pulses, and with the correct timing (PW, f). As noted earlier, the DACs can be powered between a compliance voltage VH and ground. As also noted earlier, but not shown in FIG. 4, switch matrices could intervene between the PDACs and the electrode nodes 39, and between the NDACs and the electrode nodes, to route their outputs to one or more of the electrodes, including the conductive case electrode 12 (Ec). Control signals for switch matrices, if present, may also be carried by bus 118. Notice that the current paths to the electrodes 16 include the DC-blocking capacitors 38 described earlier, which provide safety by preventing the inadvertent supply of DC current to an electrode and to a patient's tissue. Passive recovery switches 41$_i$ introduced earlier are also shown in FIG. 4.

IPG 100 also includes sensing circuitry 115, and one or more of the electrodes 16 can be used to sense neural responses such as the ECAPs described earlier. In this regard, each electrode node 39 is further coupleable to a sense amp circuit 110. Under control by bus 114, a multiplexer 108 can select one or more electrodes to operate as sensing electrodes by coupling the electrode(s) to the sense amps circuit 110 at a given time, as explained further below. Although only one multiplexer 108 and sense amp circuit 110 is shown in FIG. 4, there could be more than one. For example, there can be four multiplexer 108/sense amp circuit 110 pairs each operable within one of four timing channels supported by the IPG 100 to provide stimulation. The analog waveform comprising the ECAP is preferably converted to digital signals by one or more Analog-to-Digital converters (ADC(s)) 112, which may sample the waveform at 50 kHz for example. The ADC(s) 112 may also reside within the control circuitry 102, particularly if the control circuitry 102 has A/D inputs. Multiplexer 108 can also provide a DC reference voltage, Vamp (e.g., GND), to the sense amp circuit 110, as is useful in a single-ended sensing mode.

So as not to bypass the safety provided by the DC-blocking capacitors 38, the input to the sense amp circuitry 110 is preferably taken from the electrode nodes 39, and so the DC-blocking capacitors 38 intervene between the electrodes 16 where the ECAPs are sensed and the electrode nodes 39. However, because the DC-blocking capacitors 38 will pass AC signals while blocking DC components, the AC ECAP signal will pass through the capacitors 38 and is still readily sensed by the sense amp circuit 110. In other examples, the ECAP may be sensed directly at the electrodes 16 without passage through intervening capacitors 38.

As shown, an ECAP algorithm 124 is programmed into the control circuitry 102 to receive and analyze the digitized ECAPs. One skilled in the art will understand that the ECAP algorithm 124 can comprise instructions that can be stored on non-transitory machine-readable media, such as magnetic, optical, or solid-state memories within the IPG 100 (e.g., stored in association with control circuitry 102).

In the example shown in FIG. 4, the ECAP algorithm 124 operates within the IPG 100 to determine one or more ECAP features, which may include but are not limited to:

a height of any peak (e.g., H_N1) present in the ECAP;
a peak-to-peak height between any two peaks (such as H_PtoP from N1 to P2);
a ratio of peak heights (e.g., H_N1/H_P2);
a peak width of any peak (e.g., the full width half maximum of a N1, FWHM_N1);
an area under any peak (e.g., A_N1);
a total area (A_tot) comprising the area under positive peaks with the area under negative peaks subtracted or added;
a length of any portion of the curve of the ECAP (e.g., the length of the curve from P1 to N2, L_P1 toN2)
any time defining the duration of at least a portion of the ECAP (e.g., the time from P1 to N2, t_P1 to N2);
a time delay from stimulation to issuance of the ECAP, which is indicative of the neural conduction speed of the ECAP, which can be different in different types of neural tissues;
any mathematical combination or function of these variables (e.g., H_N1/FWHM_N1 would generally specify a quality factor of peak N1).

Once the ECAP algorithm 124 determines one or more of these features, it may then adjust the stimulation that the IPG 100 provides, for example by providing new data to the stimulation circuitry 28 via bus 118. This is explained further in U.S. Patent Application Publications 2017/0296823 and 2019/0099602, which are incorporated herein by reference in their entireties. In one simple example, the ECAP algorithm 124 can review the height of the ECAP (e.g., its peak-to-peak voltage), and in closed loop fashion adjust the amplitude of the stimulation current to try and maintain the ECAP to a desired value. The ECAP algorithm 124 can further include sub-algorithms, such as a timing algorithm 150 and an adjustment algorithm 170, which are described further below.

Figure 5A:
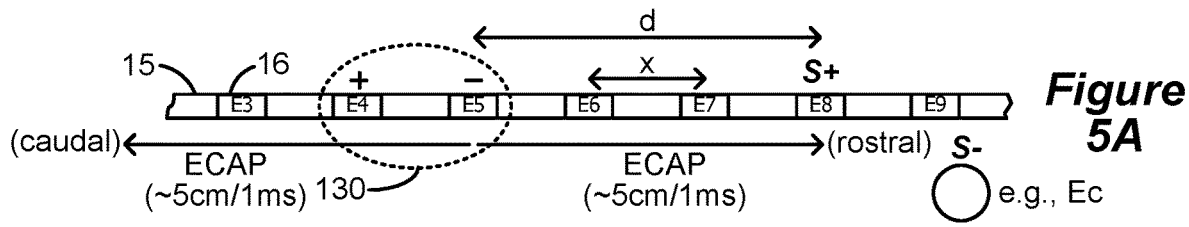
FIGS. 5A and 5B show leads producing stimulation and show differential sensing of a neural response caused by the stimulation.
Figure 5B:
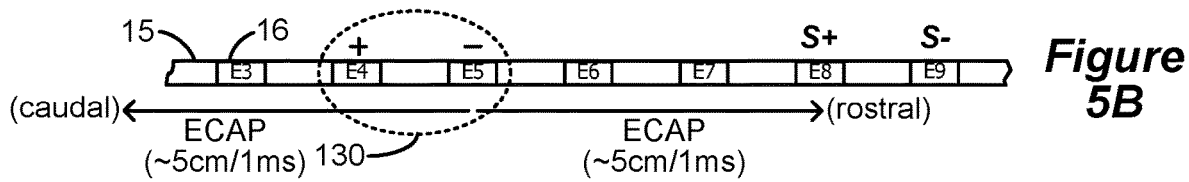

FIGS. 5A and 5B show a percutaneous lead 15 (a paddle lead 19 or other lead could also be used), and show the stimulation program example of FIG. 2A in which electrodes E4 and E5 are used to produce biphasic pulses in a bipolar mode of stimulation, with (during the first phase 30*a*) E4 comprising an anode and E5 a cathode, although other electrode arrangements (e.g., tripoles, etc.) could be used as well. Such stimulation produces an electromagnetic (EM) field 130 in a volume of the patient's tissue around the selected electrodes. Some of the neural fibers within the EM field 130 will be recruited and fire, particularly those proximate to the cathodic electrode E5. Hopefully the sum of the neural fibers firing will mask signals indicative of pain in an SCS application, thus providing the desired therapy. The recruited neural fibers in sum produce an ECAP, which can travel both rostrally toward the brain and caudally away from the brain. The ECAP passes through the spinal cord by neural conduction with a speed which is dependent on the neural fibers involved in the conduction. In one example, the ECAP may move at a speed of about 5 cm/1 ms.

The ECAP is preferably sensed differentially using two electrodes, and FIGS. 5A and 5B show different examples. In FIG. 5A, a single electrode E8 on the lead 15 is used for sensing (S+), with another signal being used as a reference (S−). In this example, the sensing reference S− comprises a more distant electrode in the electrode array 17, or (as shown) the case electrode Ec. Reference S− could also comprise a fixed voltage provided by the IPG 100, such as ground or Vamp (FIG. 4), in which case sensing would be said to be single-ended instead of differential. In FIG. 5B, two lead-based electrodes are used for sensing, with such electrodes either being adjacent or at least relatively close to one another. Specifically, in this example, electrode E8 is again used for sensing (S+), with adjacent electrode E9 providing the reference (S−). This could also be flipped, with E8 providing the reference (S−) for sensing at electrode E9 (S+). Sensing a given ECAP at different electrodes can allow the ECAP algorithm 124 to understand the time difference between the arrival of the ECAP at each of the electrodes. If the distance x between the electrodes is known, the ECAP algorithm 124 can then compute speed of the ECAP. As noted above, ECAP speed is indicative of the neural fibers involved in neural recruitment and conduction, which can be interesting to know in its own right, and which may be useful to the ECAP algorithm 124 in adjusting the stimulation provided by the stimulation circuitry 28.

Figure 6A:
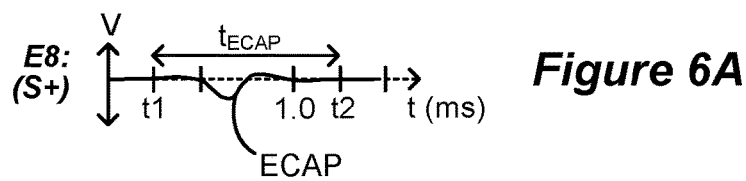

FIG. 6A shows an ECAP as ideally sensed at the sensing electrode S+ (e.g., E8). In this example, it is assumed that sensing electrode E8 is at a distance d=12 mm away from the stimulation electrodes (e.g., E5), assuming the electrodes in the array are spaced at a distance x=4 mm apart. If one assumes that the ECAP travels at a speed of 5 cm/ms (again, this could vary depending on the neural tissue involved), the ECAP would start to pass the sensing electrode S+ at a time t1=0.24 ms. The ECAP itself is also spread in time ($t_{ECSP}$). This duration is again variable, but in FIG. 6A it is assumed that the ECAP is present at the sensing electrode S+ for one millisecond as a reasonable nominal value (i.e., $t_{ECAP}$=1 ms). Therefore, the ECAP will finish passing the sensing electrode S+ in this example at a time t2=t1+$t_{ECAP}$ (e.g., t2=1.24 ms).

Figure 6B:
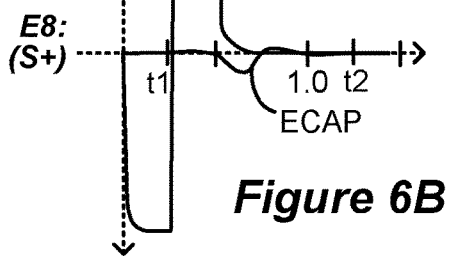
FIGS. 6B and 6C show how stimulation artifacts and passive charge recovery can interfere with sensing the neural response.

FIG. 6B shows waveforms for the stimulation program, as well as the signals that would appear in the tissue at sensing electrode E8 (S+). As well as including the ECAP signal to be sensed (between times t1 and t2), the signal at the sensing electrode S+ also includes a stimulation artifact 134. The stimulation artifact 134 comprises a voltage that is formed in the tissue as a result of the stimulation, i.e., as result of the EM field 130 produced at stimulating electrodes E4 and E5. As described in U.S. Patent Application Publication 2019/0299006, which is incorporated herein by reference in its entirety, the PDACs and NDACs used to form the currents in the tissue have high output impedances. This can cause the voltage in the tissue to vary between ground and the compliance voltage VH used to power the DACs, which as noted earlier can be a high voltage (on the order of Volts). The magnitude of the stimulation artifact 134 at a given sensing electrode S+ or its reference S− can therefore be high (e.g., from milliVolts to Volts), and significantly higher than the magnitude of the ECAP. The magnitude of the stimulation artifact 134 at the sensing electrodes S+ and S− is dependent on many factors. For example, the stimulation artifact 134 will be larger if the sensing electrodes are closer to the stimulating electrodes (E4, E5). The stimulation artifact 134 is also generally larger during the provision of the pulses (during phases 30*a* and 30*b*), although it may still be present even after the pulse (i.e., the last phase 30*b* of the pulse) has ceased due to the capacitive nature of the tissue, which keeps the electric field 130 from dissipating immediately. As shown, the polarity of the stimulation artifact 134 varies between the phases 30*a* and 30*b* of the stimulation pulses when the current reverses polarity. Although the sensing artifact 134 and the ECAP are for simplicity shown separately in FIG. 6B, in reality they would superimpose (add) at the sensing electrode S+. Note that the magnitudes of the sensing artifact 134 and the ECAP are not necessarily drawn to scale; in particular, the sensing artifact 134 may be much larger.

The relatively large-signal background stimulation artifact 134 can make resolution and sensing of the small-signal ECAP difficult at the sense amp circuit 110. To ameliorate this concern, it can be beneficial to use a sensing electrode S+ that is far away from the stimulating electrodes. See, e.g., U.S. Patent Application Publication 2020/0155019, which is incorporated herein by reference in its entirety. This can be beneficial because the stimulation artifact 134 would be smaller at a more-distant sensing electrode, and because the ECAP would pass a distant sensing electrode at a later time when the stimulation artifact 134 might have dissipated. However, using a distant sensing electrode is not always possible or practical. For one, the electrode array 17 may simply not be large enough, and therefore no electrode may be suitably far enough away from the stimulating electrodes to ideally operate as the sensing electrode. Likewise, the magnitude of the ECAP also diminishes as distance from the stimulating electrodes increases, and therefore while the stimulation artifact 134 would be smaller at a more distant sensing electrode, so too would the ECAP, again making sensing difficult.

Assume then that E8 remains the sensing electrode in FIG. 6B. In this example, it is assumed that the pulses phases 30*a* and 30*b* have relatively long pulse widths, with both PWa of the first phase 30*a* and PWb of the second phase 30*b* equaling 0.25 ms. In sum, pulses are actively driven by the DAC circuitry (40/42) from 0 to 0.5 ms, and the stimulation artifact 134 is therefore predominant during the period. (This period may include an interphase period of short duration between phases 30*a* and 30*b* although for simplicity this isn't shown). Unfortunately, this simulation artifact 134 overlaps in time with the ECAP at the sensing electrode S+, which again occurs between 0.24 (t1) and 1.24 ms (t2). This makes sensing of the ECAP difficult at the sensing electrode S+. First, the stimulation artifact 134 may be significantly larger than the small-signal ECAP. Further, the stimulation artifact 134 changes significantly during the time that the ECAP is present at the sensing electrode S+. In particular, at 0.25 ms, the stimulation artifact 134 changes polarity (from phases 30*a* to 30*b*), swinging from negative to positive values. Further, the stimulation artifact 134 falls from positive values to 0 at 0.5 ms (at the end of phase 30*b*), which in this example occurs in the middle of the ECAP. Because the ECAP is superimposed on the stimulation artifact 134, this makes resolution of the ECAP at the sense amp circuit 110 difficult.

Figure 6C:
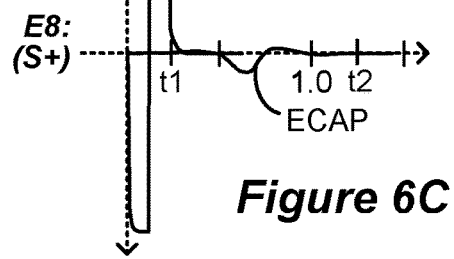

FIG. 6C alleviates this sensing problem to some extent by making the pulse widths smaller. In this example, PWa and PWb have been reduced to 0.12 ms each. As such, the stimulation artifact 134 largely ends at 0.24 ms (at the end of phase 30*b*) when the ECAP first starts to appear at the sensing electrode S+ (at t1). As such, the ECAP and stimulation artifact 134 do not significantly overlap at the sense electrode S+, and this is further true if the pulse widths are reduced further. However, this solution may not be ideal. First, adjusting the pulse widths may simply not be possible, as they may not be what is needed to provide adequate stimulation therapy for the patient. Also, simply reducing the pulse widths to avoid overlap with the ECAP may not be possible if the ECAP travels relatively fast.

Furthermore, although the ECAP may no longer overlap significantly with the stimulation artifact 134 in FIG. 6C, the ECAP does still overlap during a period 30*c* where it may be desirable to provide passive charge recovery after the active pulses phases 30*a* and 30*b* have completed. As noted earlier, passive charge recovery involving closing passive charge recovery switches 41*i* (FIG. 4), which shorts the electrode nodes ei 39 to a reference potential (such as Vbat). Even if the switch 418 at sensing electrode E8 is not closed, the effect of closing some of the switches will cause a current to passively flow in the tissue, which also causes a variable voltage artifact in the tissue as well (not shown). See, e.g., U.S. Patent Application Publication 2018/0140831. In short, passive charge recovery makes sensing of the ECAP difficult as it—like the stimulation artifact 134—can create a time varying voltage in the tissue that is significantly larger than the ECAP. Note that the provision of passive recovery 30*c* in FIG. 6B is also problematic, because there as well the passive charge recovery period 30*c* again overlaps in time with the ECAP to some extent.

Figure 7:
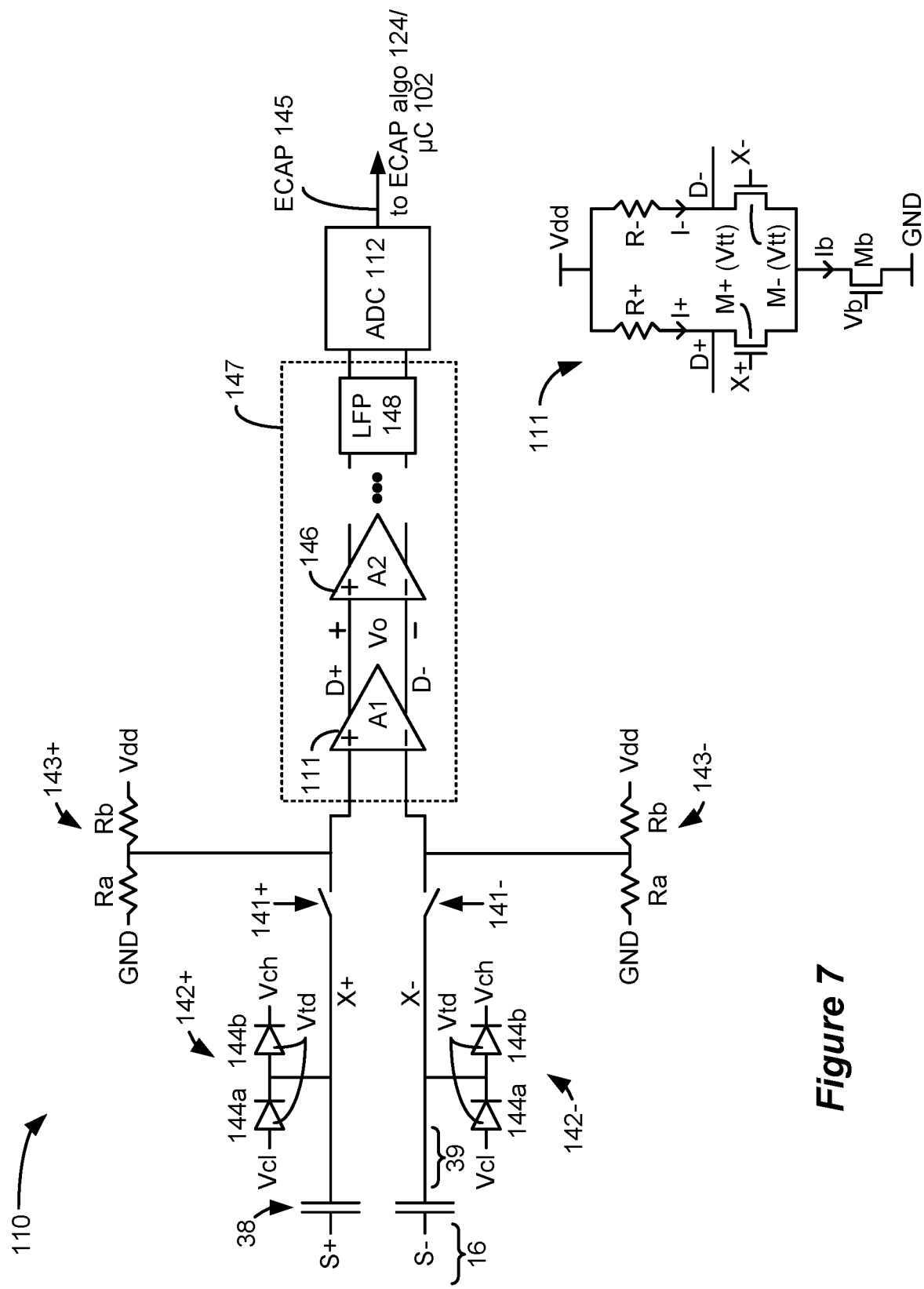
FIG. 7 shows sense amp circuity useable to sense the neural response.

As noted earlier, an ECAP is preferably sensed differentially using electrodes S+ and S−, which are both exposed to the tissue, therefore allowing the artifacts in the tissue (i.e., stimulation artifacts 134 or artifacts related to passive charge recovery) to be subtracted from the ECAP measurement to at least some degree. A sense amp circuit 110 that provides differential sensing is shown in FIG. 7. The sense amp circuit 110 includes a differential amplifier 111. Also shown is an example of the circuitry within the differential amplifier 111, although it should be noted that many different differential amplifier circuits exist and can be used in sense amp circuit 110 as well. Sensing electrode S+ and sensing reference electrode S− are coupled through the DC-blocking capacitors 38 (if used) to derive signals X+ and X− at the electrode nodes 39 that are presented to the positive and negative inputs of the differential amplifier 111. Signals X+ and X− will be largely the same as S+ and S− present at the selected sensing electrodes, but with DC signal components removed. X+ and X− are provided to the gates (control terminals) of transistors M+ and M− in the differential amplifier 111. The drains of the transistors M+ and M− are connected to differential outputs D+ and D−, which in turn are coupled to the amplifier's power supply voltage Vdd via resistances R+ and R−. The sources of the transistors M+ and M− are connected to ground as the other power supply voltage through a common bias transistor Mb, which sets the total current Ib that, in sum, can pass through each of the legs (I+, I−) of the differential amplifier. Resistances R+ and R− are equal and are represented as simple resistors, although active devices (e.g., PMOS transistors) could also be used. The output of the amplifier 111, Vo, equals the difference in the voltages at outputs D+ and D−, which in turn is influenced by the difference in the signals present at X+ and X−. Signals X+ and X−, if different (e.g., if an ECAP is present at S+), will turn transistors M+ and M− on to different degrees, thus causing different currents I+ and I− to flow through each leg. This produces different voltage drops across the resistances R+ and R−, and thus different voltages at D+ and D−. In short, Vo=D+−D−=A1(X+−X−), where A1 is the gain of the amplifier 111.

The differential amplifier 111 may provide its output to various processing circuits 147 prior to presentation to the control circuitry 102 and the ECAP algorithm 124. For example, the differential amplifier 111's differential output Vo may be provided to the inputs of another differential amplifier 146, and to still further differential amplifiers in series, etc. This can be helpful in increasing the gain of the detected ECAP signal, because the gains of each amplifier stage will multiply (A1*A2, etc.). A follower circuit or buffer could also be used in series as part of the processing circuitry 147 between the differential amplifier 111 and the ADC 112 but such stages are not shown. Further, the processing circuitry 147 may include a Low Pass Filter (LPF) 148 to remove high-frequency components in the ECAP signal that are not of interest, or that are inconsistent with the rate at which the ADC 112 will sample the signal. In one example, the LFP 148 removes frequency components of 25 kHz or higher. Processing circuitry 147 may comprise part of the control circuitry 102.

To prevent damage to or improper operation of the differential amplifier 111 (i.e., the first differential amplifier in series), inputs X+ and X− may be provided with clamping circuits 142+ and 142− respectively. In the example shown, clamping circuit 142+ comprises a serial connection of diodes 144a and 144b which are forward biased between a low clamp reference voltage reference (Vcl) and a high clamp reference voltage (Vch), and with signal X+ connected to a node between the diodes. Vcl and Vch preferably comprise ground and the power supply voltage Vdd (e.g., 3.3V). In this example, it is assumed that the diodes 144a and 114b have a forward biased threshold voltage (Vtd) of 0.6V. Diode 144a would conduct (turn on) if the voltage at X+ is less than −0.6 Volts. Because such conductance is of very low resistance, X+ is effectively clamped to a minimum of Vmin=−0.6 Volts. If it is assumed that Vdd=3.3 V, diode 144b would conduct if X+ is greater than 3.9V Volts, which would clamp X+ to a maximum of Vmax=3.9V. If the voltage at X+ is at or between −0.6 and 3.9 Volts, neither diode 144a nor 144b in clamping circuit 142+ would conduct. Clamping circuit 142− is similar, but connects to signal X−, and so similarly clamps X− to a voltage at or between −0.6 and 3.9 Volts. Modifications may be made to the clamping circuits 142+ and 142− to adjust the window of permissible voltages at which clamping does not occur. For example, Vcl and Vch could be generated by their own generator circuits to produce unique values different from ground and Vdd; different numbers of diode could be used; Zener diodes could be used that break down and thus clamp X+ or X− at specified reverse bias voltages; etc.

Also shown in FIG. 7 are blanking switches 141+ and 141− which are respectively used to pass signals at X+ and X− to the differential amplifier. Blanking switches 141+ and 141− can be used to protect the differential amplifier 111, and specifically to protect the amplifier 111 from receiving voltages that are too high at signals X+ and X−. (Note however the clamping circuits 142+ and 142−, which limit the voltages at X+ and X−, may alleviate the need for blanking switches 141+ and 141− to some degree). Blanking switches can be used in conjunction with the disclosed technique, as described further below. Note that blanking switches 141+ and 141− can comprise logic switches used to route the electrode nodes 39 to the sense amp circuit 110. For example, blanking switches 141+ and 141− can comprise switches within the multiplexer 108 (FIG. 4), or they may comprise independent switches.

The sense amp circuit 110 may further include DC-level shifting circuits 143+ and 143− to set signals X+ and X− to a DC voltage reference consistent with the input requirements for the differential amplifier 111. The differential amplifier 111 can only operate reliably if signals X+ and X− are of a magnitude that causes current I+ and I− to flow in each leg of the amplifier. In this regard, to sense the small-signal ECAP, X+ and X− should be higher than the threshold voltage of the amplifier's input transistors M+ and M− (e.g., greater than Vtt=0.7 V). It is further preferred that X+ and X− not exceed the power supply voltage Vdd of the differential amplifier (e.g., Vdd=3.3V) for proper amplifier operation. Accordingly, signals provided to the differential amplifier 111 are preferably referenced with respect to a DC voltage reference within this operating range. This reference could comprise ½ Vdd (e.g., 1.65 V), which comprises a midpoint between Vdd and ground. More preferably, the DC voltage reference could comprise ½(Vdd−Vtt)+Vtt (e.g., 2.0 V), as this value would be midpoint within the operating range 0.7V and 3.3V, and thus allow X+ and X− to symmetrically swing +/−1.3V from the reference while still providing an input magnitude suitable to operate the differential amplifier 111. While such circuits can take different forms, in the example shown the DC-level shifting circuits 143+ and 143− comprise resistor ladders, comprising resistors Ra and Rb in series biased between Vdd and ground, with signals X+ and X− connected to nodes between the resistors. This sets the DC voltage reference of both X+ and X− to Ra/(Ra+Rb)*(Vdd−ground). Thus by setting the values of Ra and Rb appropriately, the DC voltage reference can be set to any desired value between Vdd and ground, such as 2.0 V. AC signals then coupling to X+ and X−
through the capacitors 38 (such as the ECAP and/or the
stimulation artifact 134) will then be referenced to (and ride
on top off) this DC voltage reference. As a general matter,
this allows the differential amplifier 111 to be affected by the
ECAP at X+, because the superposition of the ECAP and the
DC voltage reference will cause a change in current I+.
Preferably, Ra and Rb are large resistances, such 1 Mega-
Ohm or higher.

Because the stimulation artifact 134 is present at both the
sensing electrode S+ and reference electrode S−, the differ-
ential amplifier 111 will ideally subtract artifacts in the tissue
(i.e., stimulation artifact 134 and artifacts related to passive
charge recovery) as a common mode voltage from the output
(Vo), leaving only the ECAP to be sensed. However, the
magnitude of such artifacts may not be exactly the same at
sensing electrodes S+ and S−, which is not surprising as
each is necessarily located at a different distance from the
stimulating electrodes. Thus, common mode removal of
such artifacts by the differential amplifier 111 may be not be
perfect. Furthermore, it is difficult to design the differential
amplifier 111 to resolve the ECAP when the artifacts are
both relatively large and varying over time. This is a
particular problem in the scenarios discussed earlier with
reference to FIGS. 6B and 6C, where the ECAP overlaps in
time at the sensing electrode S+ with the stimulation artifact
134 and passive recovery artifacts to significant degrees.

Conventional wisdom, as described earlier, teaches that it
is not desirable to sense an ECAP during the active provision
of pulses to the tissue. Again, this is because the stimulation
artifact 134 may be large or changing during such periods.
However, contrary to this conventional wisdom, the inven-
tors have devised a new ECAP sensing strategy, which is
shown in a first example in FIG. 8. Generally speaking, the
strategy shown in FIG. 8 senses the ECAP during the second
active charge recovery phase 30b. This phase 30b is made
longer so as to preferably entirely overlap with the ECAP at
the sensing electrode S+. This modification is shown in FIG.
8 with contrast to FIG. 6B illustrated earlier.

In FIG. 6B, the biphasic pulses comprises two phases 30a
and 30b, with phase 30a having an amplitude at electrode E4
of +Aa and a pulse width of PWa, and with phase 30b having
an amplitude of −Ab and a pulse width of PWb. (The
polarities of these currents are flipped at electrode E5).
Amplitudes |Aa| and |−Ab| can be different, as can pulse
widths PWa and PWb, but the phases 30a and 30b are
preferably charge balanced to provide for active charge
recovery as explained earlier. That is, |+Aa|*PWa=|+Q1|=|−
Ab|*PWb=|−Q|. As described earlier with respect to FIG.
6B, the timing of this pulse creates problems when sensing
an ECAP, because the stimulation artifact is large and
changing when the ECAP is present at the sensing electrode
S+.

Figure 8:
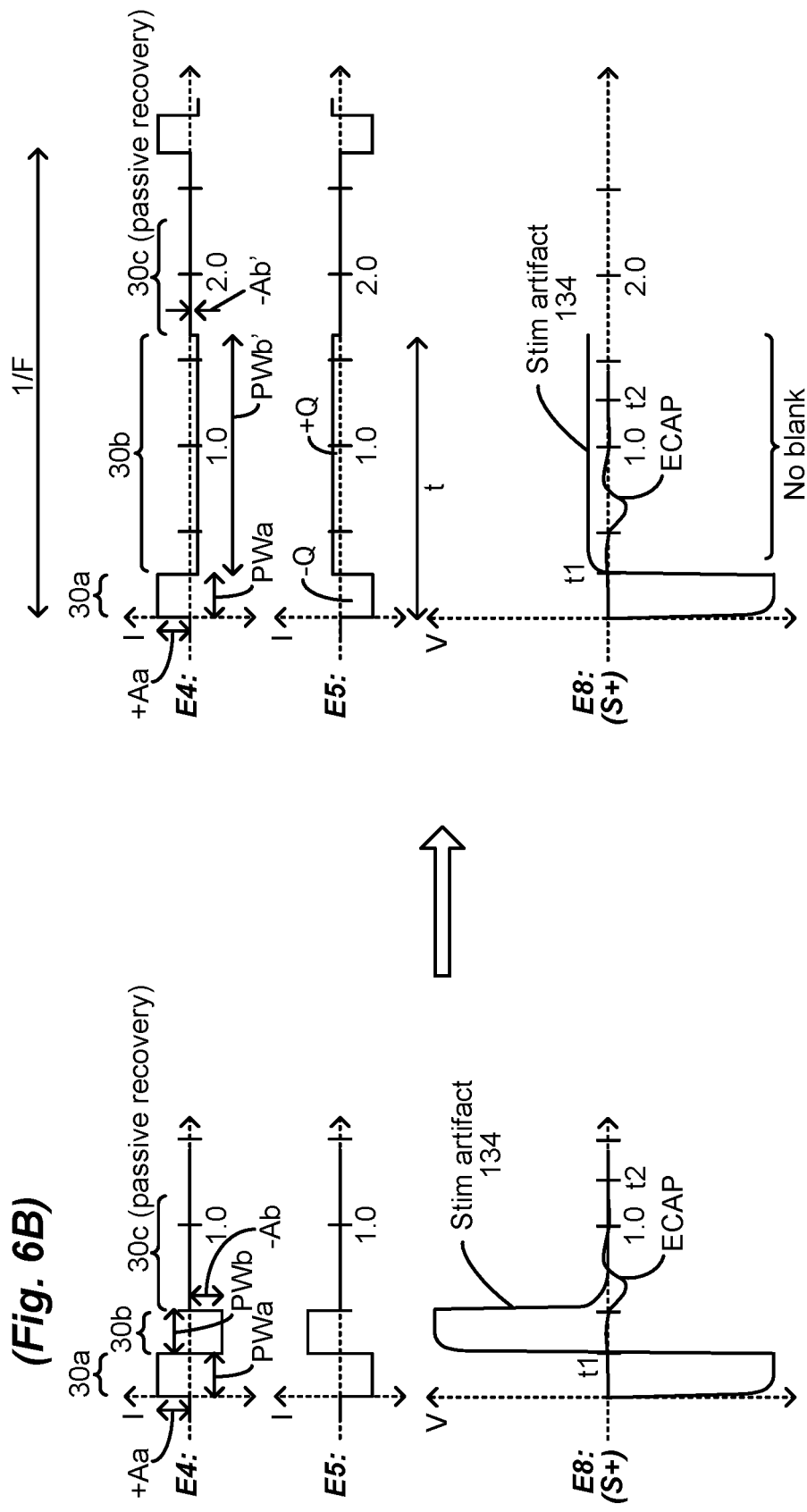
FIG. 8 shows modification of a biphasic pulse to provide a longer, lower amplitude second actively-driven pulse phase which overlaps the neural response at the sensing electrode.

Therefore, in FIG. 8, the second pulse phase 30b has been
modified. Specifically, the pulse width has been lengthened
from PWb to PWb', such that the second pulse phase 30b
now entirely overlaps the ECAP at the sensing electrode. To
keep the first and second phases 30a and 30b charge
balanced, the amplitude of the second phase 30b is accord-
ingly reduced from −Ab to −Ab', such that |+Aa|*PWa=|+
Q|=|−Ab'|*PWb'=|−Q|.

Thus, the ECAP is specifically sensed during the actively-
driven second pulse phase 30b, and hence during at least a
portion of the sensing artifact 134. This benefits ECAP
sensing in a few ways.

First, although the sensing artifact 134 is still present
during the second phase 30b when the ECAP is present at the
sensing electrode, this artifact is smaller, because the ampli-
tude of the current has been reduced from −Ab to −Ab'. This
assists sensing by the differential amplifier 111 (FIG. 7), as
the differential amplifier can more easily process (i.e., sub-
tract out) a smaller common mode voltage that is closer to
being on par with the magnitude of the ECAP.

Second, by extending the duration of the second pulse
phase 30b, this phase no longer starts or ends during (in the
middle of) the ECAP at the sensing electrode S+. This also
eases sensing because the stimulation artifact 134 is rela-
tively constant during the ECAP at the sensing electrode S+.

Third, if desired, passive recharge during period 30c can
occur after provision of the (extended) second pulse phase
30b. At this point, the ECAP has already been sensed, and
thus passive charge recovery can occur without conflict to
ECAP sensing.

Fourth, stimulation therapy to the patient is not signifi-
cantly altered. Generally, the first phase 30a of a biphasic
pulse creates significant therapeutic effect in the patient, and
thus the amplitude Aa and pulse width PWa are generally
tailored for the patient. In this example, these pulse param-
eters Aa are PWa not altered. The second pulse phases 30b,
while necessary for active charge recovery, is generally not
therapeutically significant and thus can be changed without
significant impact to the patient.

Note that there can be practical limits to the solution of
FIG. 8. For example, if the pulses are of high frequency F,
there may not be sufficient time between subsequent pulses
to fit an extended second pulse phase 30b (and possibly also
a passive recovery period 30c). However, this problem can
simply be mitigated by not providing a subsequent pulse
until after ECAP measurement has completed. This should
not be significantly problematic to patient therapy, as ECAP
measurements would normally not be taken after each pulse,
but instead only need to be taken occasionally; occasionally
delaying or missing a therapeutic pulse will not significantly
affect stimulation therapy. It may also be the case that the
ECAP overlaps with the first pulse phase 30a at the sensing
electrode S+, i.e., t1 may be smaller than PWa. This could
impair ECAP sensing. However, given the timings normally
involved in stimulation therapy, such overlaps would not be
frequent as a practical matter, and could be mitigated in
other manners, such as by choosing a sensing electrode S+
that is farther from the stimulating electrodes.

In the disclosed technique, as shown in FIG. 8, blanking
should not occur during the second pulse phases 30b when
the ECAP is sensed. That is, switches such as 141+ and 141−
(FIG. 7) to the inputs of the differential amplifier 111 should
be closed to allow sensed signals S+ and S− (and X+ and
X−) to reach the inputs to the amplifier. During first phase
30a, blanking can occur—i.e., switches 141+ and 141− can
be opened. This can help protect the differential amplifier
111 from saturating, which may occur if the stimulation
artifact 134 is large during the first phase. That being said,
it is not strictly necessary to blank during the first phase 30a,
particularly if clamping circuits 142+ and 142− are used to
limit the voltages on X+ and X−.

Figure 9:
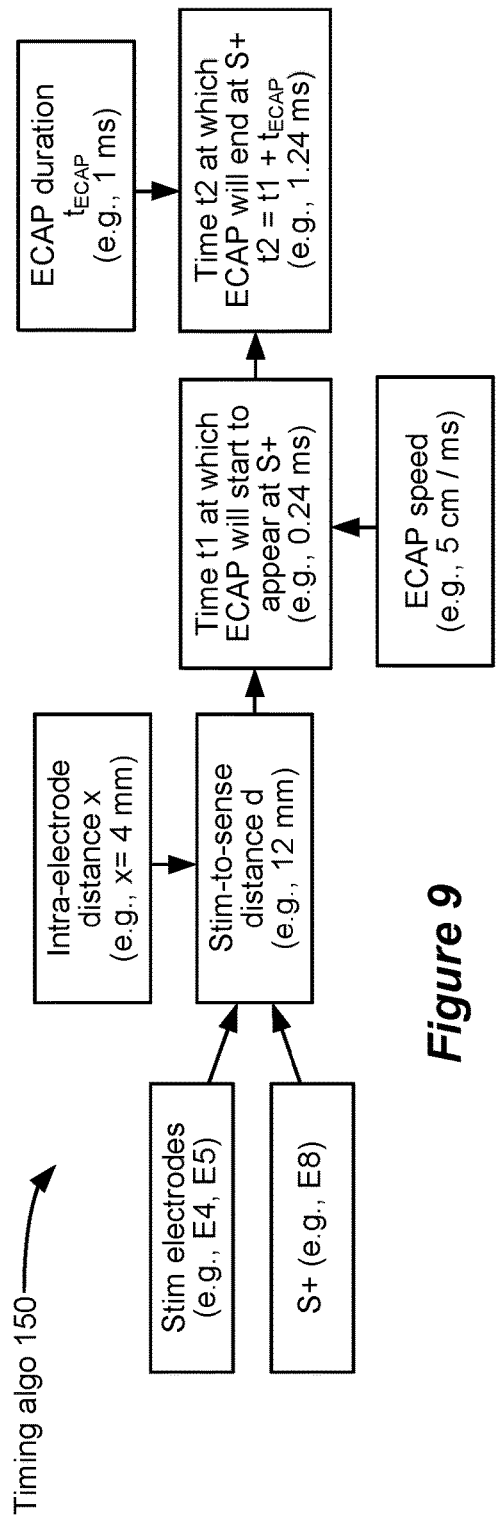
FIG. 9 shows a timing algorithm operable to determine when a neural response starts and stops at a sensing electrode.
Figure 10A:
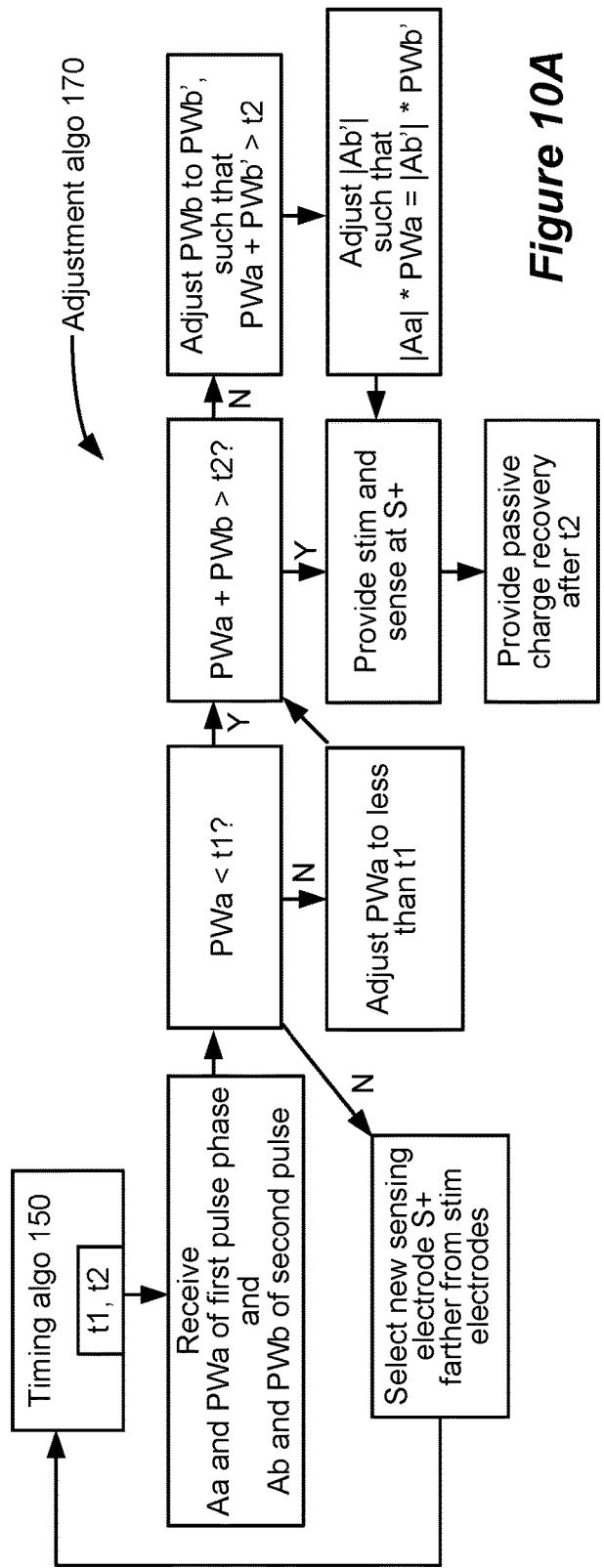
FIGS. 10A and 10B show adjustment algorithms useable in conjunction with the timing algorithm to ensure that the second pulse phase will overlap the neural response at the sensing electrode.
Figure 10B:
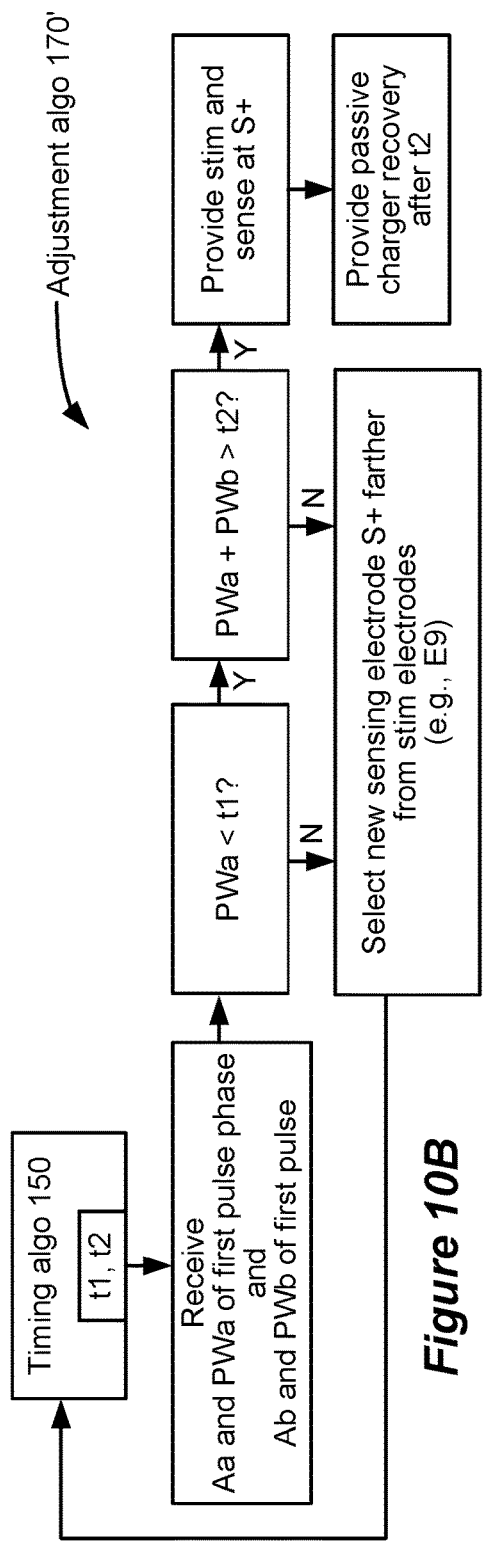

FIGS. 9 through 10B disclose optional algorithms 150,
170, and 170' that can be used to adjust the second pulse
phase 30b to assist with ECAP sensing. FIG. 9 discloses a
timing algorithm 150 which determines when an ECAP will
start (t1) and finish (t2) appearing at a sensing electrode S+
that has been chosen for ECAP sensing. The timing algo-
rithm 150 can receive as inputs, or be programmed with, the
selected sensing electrode(s) (e.g., S+=E8) and stimulating
electrodes (e.g., E4, E5), and the distance (x) between
electrodes in the electrode array (e.g., 4 mm). From this, the algorithm 150 can compute the distance (d) between the stimulation and sensing electrodes (e.g., 12 mm). The timing algorithm 150 can also receive, or be programmed with, an expected ECAP speed (e.g., 5 cm/ms). Note that this speed can be an estimated speed, or a speed that is actually measured by the IPG. From distance d and the ECAP speed, a time t1 at which the ECAP will first appear at the sensing electrode can be determined (e.g., d/speed=0.24 ms). The timing algorithm 150 can also receive, or be programmed with, an expected ECAP duration ($t_{ECAP}$=1 ms). Again, this value can also be measured in the IPG. This allows a time t2 at which the ECAP will finish appearing at the electrode to be computed (e.g., t2=t1+$t_{ECAP}$). If necessary, t1 and t2 can also be adjusted to provide additional margin—e.g., t1 can be slightly lowered and t2 can be slightly increased to ensure that t1 and t2 are suitable for detecting the ECAP (using adjustment algorithm 170 which follows).

Although not shown, timing algorithm 150 may also determine t1 and t2 using measurements alone. For example, short test pulses of low pulse widths can be used which are unlikely to produce significant artifacts, with the resulting ECAP measured by the sense amp circuitry 110. Thus, t1 and t2 may be determined empirically.

Once t1 and t2—the start and finish of the ECAP at the sensing electrode S+—have been determined using timing algorithm 150, an adjustment algorithm 170 may use these values to determine how to adjust a prescribed pulse, as shown in FIG. 10A. In particular, adjustment algorithm 170 can adjust the second active-recovery phase 30b to ensure that it is long enough to overlap with the ECAP at the sensing electrode S+. In this regard, pulse parameters for a prescribed biphasic pulse—presumably a pulse determined to provide adequate patient therapy—are received, which in this example comprises parameters for a first phase 30a (Aa, PWa), and a second phase 30b (Ab, PWb). It is assumed in this example that such a prescribed pulse is charge balanced, as discussed above.

The adjustment algorithm 170 as first step can, optionally, assess the timing of the first pulse phase (PWa) to determine whether it is smaller than t1. As discussed earlier, if PWa is not smaller than t1, this can be problematic to ECAP sensing, because the ECAP would be present at the sensing electrode S+ when the stimulation artifact 134 is changing (between phases 30a and 30b). If PWa is not less than t1, the adjustment algorithm 170 could take certain actions, such as adjusting PWa to make it less than t1 (even though this could change the therpay provided by first phase 30a), or choosing a new sensing electrode S+ that might be further away from the stimulating electrodes (as discussed next with respect to FIG. 10B). This step may not be necessary if it is known a priori that PWa<t1, and therefore that the ECAP should not overlap with the first phase 30a of the pulse. Note that choosing a new sensing electrodes would change the timing t1 and t2 at which the ECAP would start and finish at that new sensing electrode, and therefore the newly chosen sensing electrode S+ can be passed back to the timing algorithm 150 (FIG. 9) so that t1 and t2 can be re-determined, and adjustment algorithm 170 repeated.

If PWa<t1, the adjustment algorithm 170 can continue by assessing whether the duration of both pulse phases is less than t2, i.e., if PWa+PWb>t2. (Alternatively, if a significant interphase period IP is used between phases 30a and 30b, the algorithm 170 can inquire whether PWa+IP+PWb>t2). If this is true, then the ECAP at the sensing electrode should fall entirely within the prescribed second phase 30b. In this case, the IPG can simply provide the stimulation, and sense the ECAP during the second pulse phase 30b at the sensing electrode S+, similarly to what was shown in FIG. 8. Passive charge recovery during period 30c can then be performed after the second pulse phase 30 is complete, which will not conflict with the already-sensed ECAP.

If PWa+PWb is not greater than t2, this means that the second phase 30b ends somewhere in the middle of when the ECAP is expected to be present at the sensing electrode S+, which as noted earlier can be problematic because the stimulation artifact 134 would be changing during the transition. The adjustment algorithm 170 can thus adjust the timing of the second phase 30b by increasing PWb to PWb' so that PWa+PWb' is now greater than t2. At this point, the ECAP at the sensing electrode should fall entirely within the adjusted second phase 30b. The adjustment algorithm 170 can then adjust the amplitude of the second phase 30b to ensure that the adjusted second phase 30b is charge balanced with the first phase 30a. Thus, a new (lower) amplitude |Ab'| is chosen for the second phase such that |Aa|*PWa=|Ab'|*PWb'—i.e., |Ab'| is set equal to |Aa|*PWa divided by the adjusted pulse width PWb'. After this adjustment to the second phase 30b is made, the IPG can provide the stimulation, and sense the ECAP during the adjusted second pulse phase 30b at the sensing electrode S+, followed by passive charge recovery 30c if desired.

Although algorithms 150 and 170 are described as separate for ease of illustration, they could be combined into a single algorithm.

FIG. 10B shows an alternative adjustment algorithm 170' which can alternatively change the selected sensing electrode S+ to ensure that the ECAP is present at the sensing electrode during the entirety of the second phase 30b. If PWa is not less than t1, or if PWa+PWb is not greater than t2, the adjustment algorithm 170' can choose a new sensing electrode (e.g., E9) that is farther from the stimulating electrodes. Again, choosing a new sensing electrodes would change timings t1 and t2, and therefore the newly chosen sensing electrode S+ can be passed back to the timing algorithm 150 (FIG. 9) so that t1 and t2 can be re-determined, and adjustment algorithm 170' repeated. After such iteration(s), if PWa is less than t1, and if PWa+PWb is greater than t2, then the ECAP should be present at the (new) sensing electrode S+ during the second phase 30b, and so stimulation and sensing can be provided, followed by passive charge recovery.

Although not shown in the figures, realize that adjustment algorithms 170 (FIG. 10A) and 170' (FIG. 10B) can each be run, or run concurrently, with 170 being used to adjust the second pulse phase 30b, and 170' adjusting the sensing electrode S+. As such, adjustment using algorithms 170 and 170' can be an iterative process, with the effect of ensuring that the ECAP will be present and easily sensed at the sensing electrode S+ during the second phase 30b, as per FIG. 8.

Figure 11:
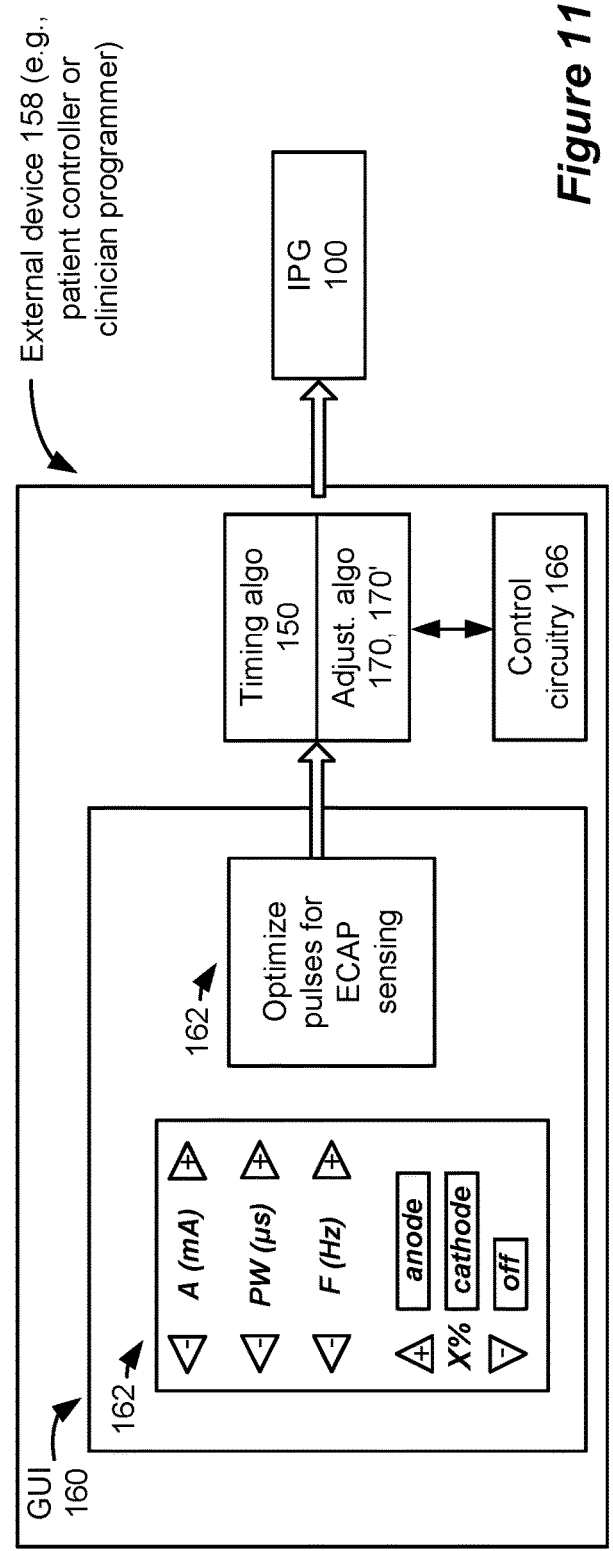
FIG. 11 shows operation of the timing and adjustment algorithms in an external device in communication with the IPG.

As shown in FIG. 4, the timing and adjustment algorithms can comprise part of the ECAP algorithm 124 operable in the control circuitry 102 (FIG. 4). However, these algorithms can also operate in whole or in part in external computer devices 158 that are used to program the IPG, such as a patient's external controller or a clinician programmer. Such external devices 158 typically wirelessly communicate with an IPG 100, and are described in U.S. Patent Application Publication 2019/0046800, which is incorporated herein by reference in its entirety. A Graphical User Interface (GUI) 160 as rendered on such an external device 158 is shown in FIG. 11. Shown in GUI 160 are user selectable options 162 to set stimulation parameters for the pulses or pulse phases of IPG, such as amplitude (A), pulse width (PW), and frequency (F), as well as whether certain electrodes are to operate as anodes or cathodes, and a percentage of the amplitude (X %) to be applied to that electrode. In reality, the GUI 160 and 162 may be much more complicated than what is shown.

The GUI 160 can include an option 164 to modify pulses otherwise prescribed into pulses better suited to ECAP sensing—such as by adding a second pulse phase 30b, or modifying an already—prescribed second pulse phase 30b, to overlap with the ECAP at the sensing electrode as shown in FIG. 8 and in other subsequent examples. Selection of option 164 may use the timing and adjustment algorithms of FIGS. 9-10B, or other algorithms, to determine the necessary pulse parameters to achieve this goal, and to send these pulse parameters to the IPG. If necessary, the IPG may communicate ECAP test measurements back to the algorithms, such as ECAP start and finish times t1 and t2 as measured at the sensing electrode S+. The algorithms can be stored in non-transitory machine-readable media in the external device 158, such in as magnetic, optical, or solid-state memories, which may be stored in association with the external device 158's control circuitry 166, which may comprise one or more microcontrollers, microprocessors, FPGAs, DSPs, etc. In one example, control circuitry 166 can comprise one of the i5 family of microprocessors, as manufactured by Intel Corp.

Figure 12:
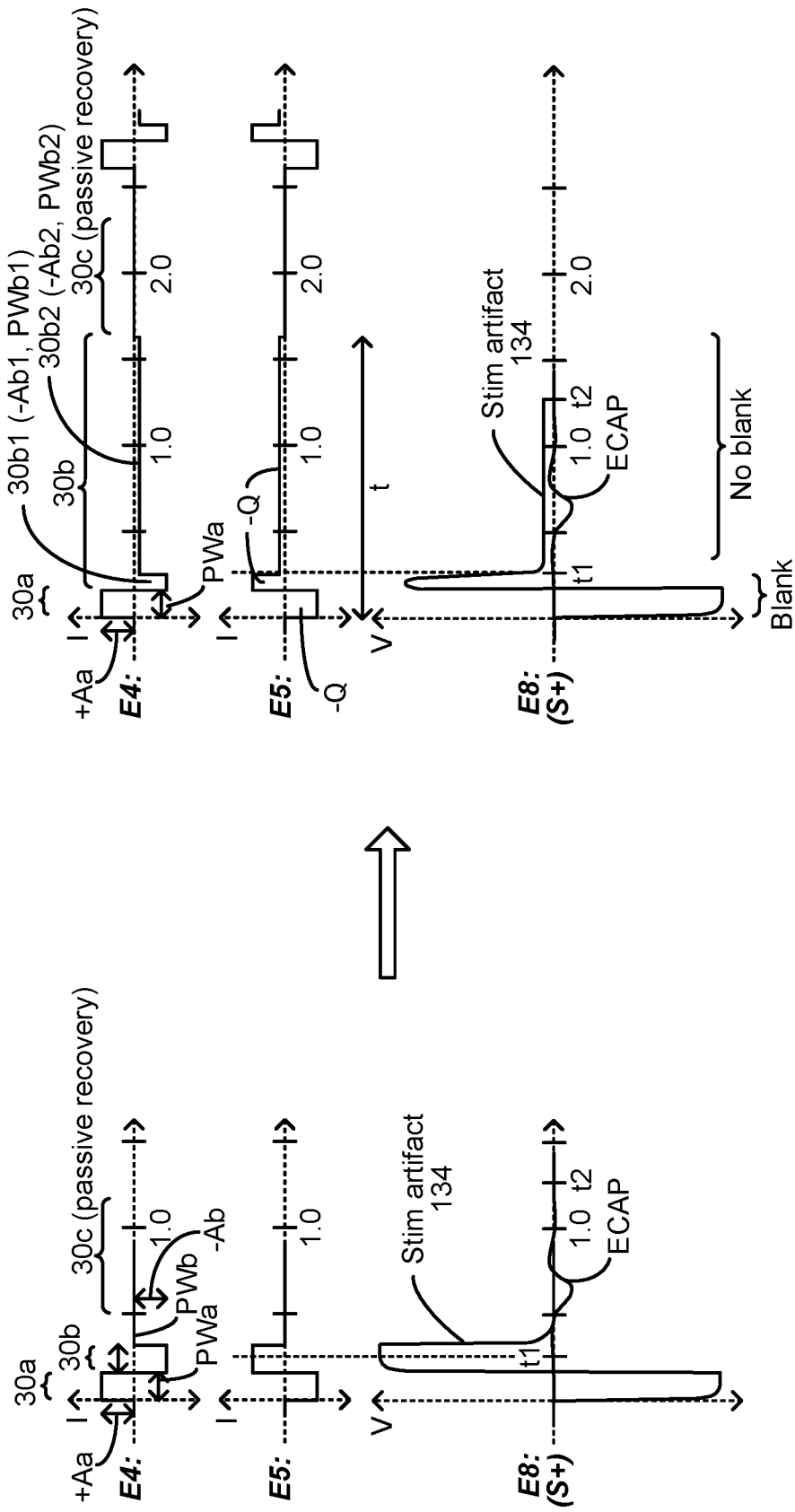
FIG. 12 shows a modification in which the second phase is split into two different sub-phases of different amplitudes, with the neural response sensed during the lower-amplitude sub-phase.

FIG. 12 shows another manner in which the second pulse phase 30b can be adjusted, and specifically shows adjustment of only a portion of the second phase 30b. The left of FIG. 12 shows pulses prior to adjustment, and notice in this situation that the ECAP starts to be present at the sensing electrode (t1) in the middle of the second pulse phase 30b.

In this circumstance, the second pulse phase 30b can be split into two sub-phases 30b1 and 30b2. Sub-phase 30b1 can precede t1 (with a pulse width of PWb1), and—because the ECAP is not yet present at the sensing electrode S+—can be larger in magnitude. For example, if phase 30b prior to adjustment has a magnitude of |−Ab|, the magnitude during sub-phase 30b1 can be |−Ab1|, which may equal un-adjusted amplitude |−Ab|, or be smaller or larger, but still relatively large. This allows a significant portion of charge injected during the first phase 30a (|Aa|*PWa=|+Q|, at E4), but perhaps not all, to be actively recovered during this sub-phase 30b1.

Sub-phase 30b2 starts at or before t1, when the ECAP would start to be present at the sensing electrode S+. Sub-phase 30b2 should continue for a duration (PWb2) sufficient to cover the ECAP at the sensing electrode—i.e., sub-phase 30b2 should last at least until t2 when the ECAP is finishing at the sensing electrode S+. The amplitude |−Ab2| of sub-phase 30b2 may be set to ensure that sub-phases 30b1 and 30b2 are charge balanced with the first phase 30a. In other words, once Ab1, PWb1 and PWb2 are set, amplitude Ab2 is selected such that |+Aa|*PWa=|Ab1|*PWb1+|−Ab2|*PWb2. Notice that splitting second phase 30b into sub-phases 30b1 and 30b2 can allow the amplitude of stimulation during the ECAP—i.e., |Ab2|—to be significantly reduced. This reduces the magnitude of the stimulation artifact 134 during ECAP sensing, which makes such sensing easier. Notice also that the stimulation artifact 134 is not significantly changing during sub-phase 30b2 when the ECAP is being sensed.

Figure 13A:
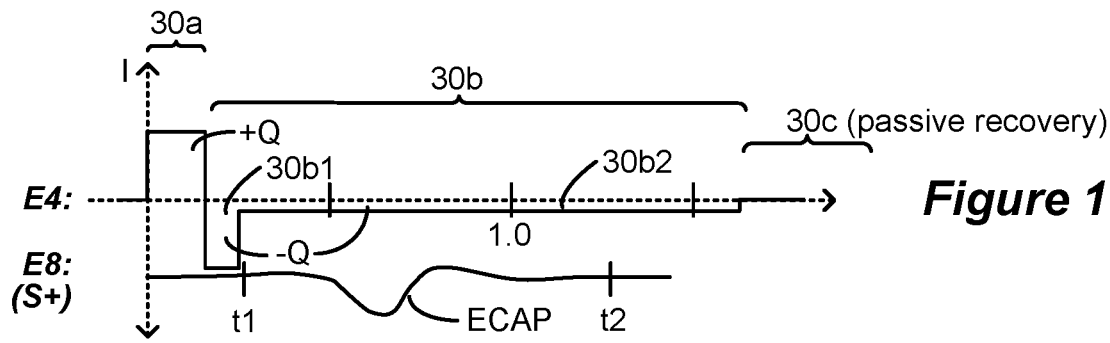
FIGS. 13A-13D show different examples in which the neural response can be sensed during the lower-amplitude sub-phase.
Figure 13B:
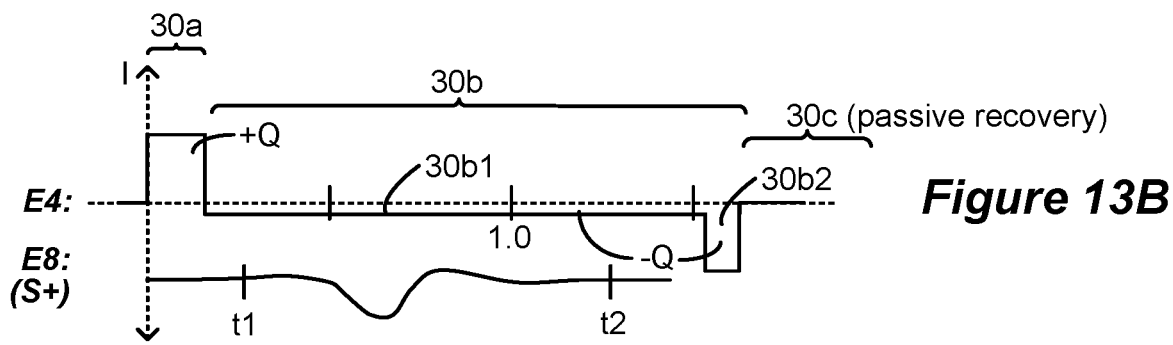

FIGS. 13A-13D show different examples similar to FIG. 12 in which the second phase 30b is divided into sub-phases having different amplitudes and durations. FIG. 13A shows the example of FIG. 12 again, showing only the pulse as present at electrode E4 and the ECAP at sensing electrode E8 (artifacts not shown). FIG. 13B shows that a lower-amplitude sub-phase 30b1 can precede a higher-amplitude sub-phase 30b2. This allows the ECAP to be sensed during sub-phase 30b1 when the stimulation artifact would be lowest, and so sub-phase 30b1 in this instance is long enough to completely overlap with the ECAP at the sensing electrode S+. Higher-amplitude sub-phase 30b2 will provide the majority of active charge recovery after the sub-phase 30b1, thus allowing phase 30a to be charge balanced with the sum of sub-phases 30b1 and 30b2.

Figure 13C:
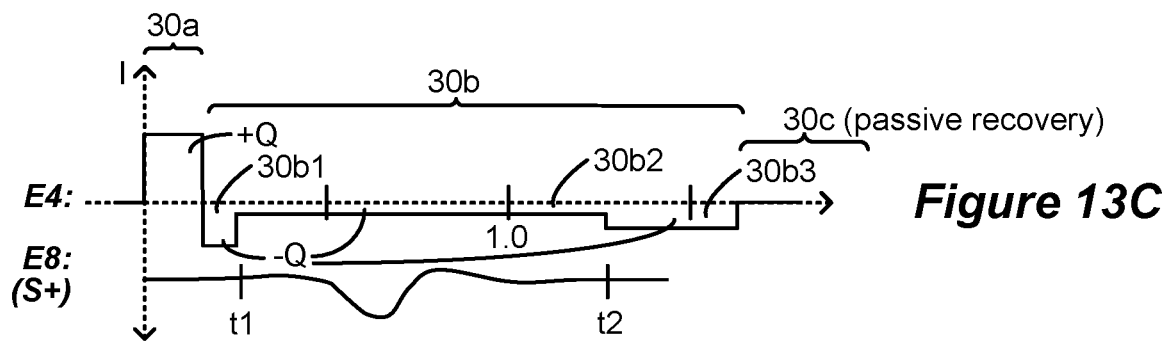

In FIG. 13C, phase 30b is split into three sub-phases 30b1, 30b2, and 30b3. Sensing of the ECAP occurs during the middle sub-phase 30b2, which preferably has the lowest amplitude of the sub-phases, and hence will result in the lowest stimulation artifact 134. Higher-amplitude sub-phases 30b1 and 30b2 respectively precede and follow sub-phase 30b2, thus allowing the majority of active charge recovery to occur during those sub-phases. Again, the pulse is charge balanced, with the charge during phase 30a equaling the sum of the charge at phases 30b1, 30b2, and 30b3.

Figure 13D:
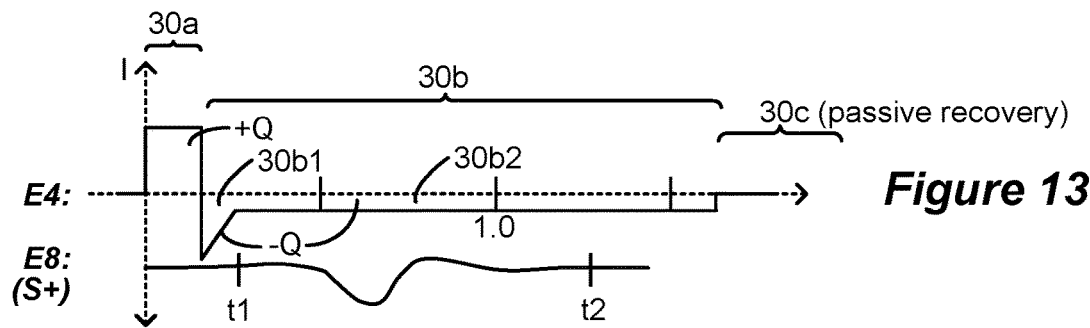

FIG. 13D is similar to FIG. 13A, but shows that the current need not be constant during the higher amplitude sub-phases. In this example, the current during higher-amplitude sub-phase 30b1 is not constant, and this could also be true for the higher-amplitude sub-phases of FIGS. 13B and 13C as well. The current may also not be constant during the lower-amplitude sub-phase 30b2 when the ECAP is sensed, but a constant current is preferable so that the stimulation artifact 134 will be relatively constant, which as noted earlier eases ECAP sensing. In all of the examples of FIGS. 13A-13D, passive charge recovery 30c can follow the second pulse phase 30b. Note also that the amplitude of the first phase 30a does not have to be constant in any of the examples disclosed herein.

Figure 14A:
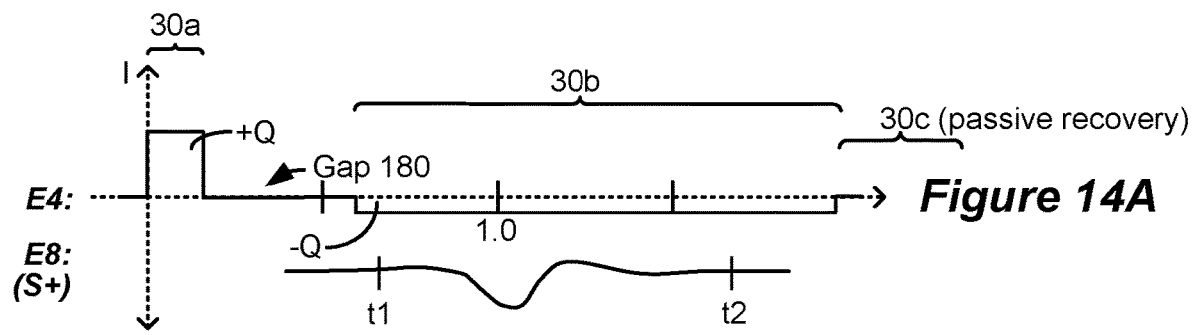
FIGS. 14A and 14B show examples in which a longer-duration gap occurs between the first and second pulse phases.
Figure 14B:
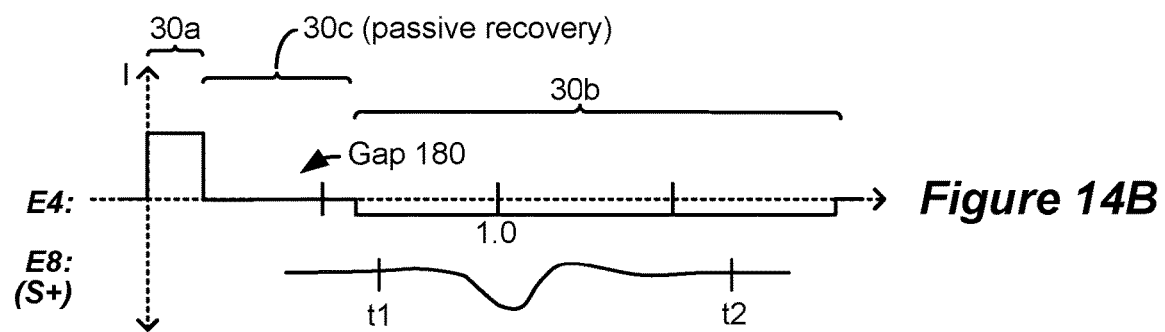

FIGS. 14A and 14B show that there can be a significant gap 180 in time between the first and second pulse phases 30a and 30b during which no active charge is driven by the DAC circuitry (40/42; FIG. 4). This gap 180 can be significantly longer than the short interphase period that is typically present between first and second phases 30a and 30b in a biphasic pulse. Use of a longer gap 180 can be warranted if the ECAP will reach the sensing electrodes at later times—i.e., if t1 and t2 are longer. In this instance, the second pulse phase 30b is timed to again cover the ECAP at the sensing electrode. In FIG. 14A, nothing occurs during the gap 180, and passive charge recovery 30c occurs after the second phase 30b. In FIG. 14B, passive charge recovery 30c occurs during at least a portion of the gap 180. This allows some charge injected during the first phase 30a to be passively recovered prior to active charge recovery that would occur during the second active phase 30b. Passive charge recovery could also occur (or continue) after the second phase 30b in FIG. 14B, although this isn't shown.

It should be noted that use of an extended second phase 30b as shown in various examples need not result from the modification of an otherwise initial biphasic pulse. Instead, extended second pulse phases 30b may be added to monophasic pulses. Thus, in the various examples, only monophasic pulses 30a may be prescribed, with extended second active phases 30b of low amplitude added specifically for the purpose of assisting in ECAP sensing. It can be useful to add such second phases 30b to monophasic pulses simply for the purpose of producing a smaller constant stimulation artifact 134 more conducive with ECAP sensing. Further, while it may be preferable that the actively-driven second phase 30b always be charge balanced with the actively-driven first phase 30a, these phases may also not be charge balanced, and this is particularly true if passive charge recovery 30c is used to recover any remaining charged not actively recovered. Further, and realizing that passive charge recovery can be used, it is not strictly necessary that the first and second pulses phases 30a and 30b be of differing polarities at the electrodes, although this is preferred to provide at least some amount of active charge recovery. While first pulse phase 30a is preferably actively driven, this is not strictly required, and instead the first pulse phase 30a can be passively driven as well.

As noted earlier, an ECAP is just one example of a neural response that can be sensed using the disclosed techniques.

Although particular embodiments of the present invention have been shown and described, the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A stimulator device, comprising:
   a plurality of electrode nodes, each electrode node configured to be coupled to one of a plurality of electrodes configured to contact a patient's tissue;
   stimulation circuitry configured to form stimulation at at least two of the electrode nodes, wherein the stimulation at each of the two electrode nodes comprises a pulse comprising a first phase followed by a second phase;
   sensing circuitry configured to sense a neural response to the stimulation at at least one sensing electrode node each comprising one of the electrode nodes; and
   control circuitry configured to determine a timing at which the neural response will be present at at least one of the sensing electrode nodes, and to adjust a duration of the second phase in accordance with the determining timing.

2. The stimulator device of claim 1, wherein the control circuit is configured to adjust the duration of the second phase such that the sensing circuitry is configured to sense the neural response during the second phase.

3. The stimulation device of claim 2, wherein the sensing circuitry is configured to sense an entire duration of the neural response during the second phase.

4. The stimulation device of claim 1, wherein the at least one sensing electrode node is selectable.

5. The stimulation device of claim 1, wherein the sensing circuitry comprises a differential amplifier having first and second inputs, and wherein the differential amplifier receives one of the sensing electrode nodes at each of the first and second inputs.

6. The stimulation device of claim 5, further comprising a conductive case for housing the stimulation circuitry and the sensing circuitry, wherein the conductive case comprises one of the plurality of electrodes, and wherein the case electrode is coupled to one of the sensing electrode nodes received by the differential amplifier.

7. The stimulation device of claim 1, wherein the first phase is of an opposite polarity to the second phase at each of the at least two electrode nodes.

8. The stimulation device of claim 7, wherein the first and second phases are charge balanced at each of the at least two electrodes.

9. The stimulation device of claim 7, wherein the first and second phases are not charge balanced at each of the at least two electrodes.

10. The stimulation device of claim 1, wherein the control circuitry is further configured to adjust an amplitude of the second phase.

11. The stimulation device of claim 10, wherein the control circuitry is configured to adjust the duration and the amplitude of the second phase such that the second phase is charge balanced with the first phase at each of the at least two electrodes nodes.

12. The stimulation device of claim 11, wherein the control circuitry to configured to adjust the duration of the second phase so that it is longer than a duration of the first phase, and to adjust the amplitude of the second phase such that it is smaller than an amplitude of the first phase.

13. The stimulation device of claim 1, wherein the stimulation circuitry is configured to actively drive a current during the second phase.

14. The stimulation device of claim 13, wherein the current comprises a constant current.

15. The stimulation device of claim 13, wherein the stimulation circuitry is configured to actively drive a current during the first phase.

16. The stimulation device of claim 13, wherein the stimulation circuitry comprises a plurality of passive charge recovery switches each coupled between one of the electrode nodes and a reference potential.

17. The stimulation device of claim 16, wherein the stimulation circuitry is further programmed to provide passive charge recovery after the second phase by closing at least the passive recovery switches coupled to the at least two electrode nodes.

18. A method for operating a stimulator device, the stimulator device comprising a plurality of electrode nodes, each electrode node configured to be coupled to one of a plurality of electrodes configured to contact a patient's tissue, the method comprising:
   providing stimulation at at least two of the electrode nodes, wherein the stimulation at each of the two electrodes comprises at least one pulse comprising a first phase followed by a second phase; and
   sensing a neural response to the stimulation at at least one sensing electrode node each comprising one of the electrode nodes, wherein the neural response is present at the sensing electrode node for a duration,
   wherein the neural response is sensed during the second phase.

19. The method of claim 18, wherein the first phase is of an opposite polarity to the second phase at each of the at least two electrode nodes.

20. The method of claim 19, wherein a duration of the second phase is longer than a duration of the first phase, and wherein an amplitude of the second phase is smaller than an amplitude of the first phase.

* * * * *